US012605400B2

(12) United States Patent
Li et al.

(10) Patent No.: US 12,605,400 B2
(45) Date of Patent: Apr. 21, 2026

(54) OLIGOMERIC NUCLEIC ACID MOLECULE, AND APPLICATION THEREOF IN AN ACUTE INTERMITTENT PORPHYRIA TREATMENT

(71) Applicant: Ractigen Therapeutics, Nantong City (CN)

(72) Inventors: Longcheng Li, Nantong City (CN); Moorim Kang, Nantong City (CN)

(73) Assignee: RACTIGEN THERAPEUTICS, Nantong City (CN)

( * ) Notice: Subject to any disclaimer, the term of this patent is extended or adjusted under 35 U.S.C. 154(b) by 1145 days.

(21) Appl. No.: 17/594,740

(22) PCT Filed: Apr. 29, 2020

(86) PCT No.: PCT/CN2020/087844
§ 371 (c)(1),
(2) Date: Oct. 28, 2021

(87) PCT Pub. No.: WO2020/221309
PCT Pub. Date: Nov. 5, 2020

(65) Prior Publication Data
US 2022/0211739 A1　　Jul. 7, 2022

(30) Foreign Application Priority Data

Apr. 30, 2019　(CN) ......................... 201910364093.9

(51) Int. Cl.
| | |
|---|---|
| *A61K 31/713* | (2006.01) |
| *A61P 3/00* | (2006.01) |
| *A61P 7/00* | (2006.01) |
| *C12N 5/10* | (2006.01) |
| *C12N 15/113* | (2010.01) |

(52) U.S. Cl.
CPC .............. *A61K 31/713* (2013.01); *A61P 3/00* (2018.01); *A61P 7/00* (2018.01); *C12N 5/10* (2013.01); *C12N 15/1137* (2013.01)

(58) Field of Classification Search
None
See application file for complete search history.

(56) References Cited

U.S. PATENT DOCUMENTS

| | | | |
|---|---|---|---|
| 9,669,109 B1 | 6/2017 | Pagani | |
| 2007/0031844 A1* | 2/2007 | Khvorova ................. | A61P 3/10 435/6.13 |
| 2007/0292408 A1 | 12/2007 | Singh | |
| 2010/0210707 A1 | 8/2010 | Li | |
| 2013/0164846 A1 | 6/2013 | Saetrom | |
| 2015/0104869 A1 | 4/2015 | Li | |
| 2015/0126578 A1 | 5/2015 | Place | |
| 2017/0044540 A1 | 2/2017 | Sætrom | |
| 2018/0305689 A1 | 10/2018 | Sætrom et al. | |
| 2020/0255827 A1 | 8/2020 | Huber | |

| | | |
|---|---|---|
| 2021/0332366 A1 | 10/2021 | Li |
| 2022/0064642 A1 | 3/2022 | Li |
| 2022/0096350 A1 | 3/2022 | Li |
| 2022/0096516 A1 | 3/2022 | Kang |
| 2022/0313721 A1 | 10/2022 | Li |
| 2023/0212565 A1 | 7/2023 | Li |
| 2023/0220389 A1 | 7/2023 | Li |

FOREIGN PATENT DOCUMENTS

| | | |
|---|---|---|
| CN | 1904900 A | 1/2007 |
| CN | 101990433 A | 3/2011 |
| CN | 102947451 A | 2/2013 |
| CN | 104173386 | 12/2014 |
| CN | 104583398 A | 4/2015 |
| CN | 104630219 A | 5/2015 |
| CN | 106032532 A | 10/2016 |
| CN | 106480028 A | 3/2017 |
| CN | 106929508 A | 7/2017 |
| CN | 107446927 A | 12/2017 |
| CN | 108103063 A | 6/2018 |

(Continued)

OTHER PUBLICATIONS

Chen Zhong et al., "Recent Advances in RNA Activation", Journal of Contemporary Urologic and Reproductive Oncology, (Apr. 22, 2012), vol. 4, No. 2, pp. 65-67.
Chen, Hong, "The Role of Small RNA Induced INTS6 Gene Activation in Castration Resistant Prostate Cancer," Chinese Doctoral Dissertations Full-text Database, Medicine and Health Sciences, No. 11, pp. 31-41, Nov. 15, 2013.
Eastham et al., "In Vivo Gene Therapy with p53 or p21 Adenovirus for Prostate Cancer," Cancer Res, vol. 55, pp. 5151-5155 (1995).
Elbashir et al. (The EMBO Journal, vol. 20, No. 23, pp. 6877-6888, 2001).
Fang, et al., "p21 Waf1/cip1/sdi1 induces permanent growth arrest with markers of replicative senescence in human tumor cells lacking functional p51," Oncogene, vol. 18, pp. 2789-2797, (1999).
Ghersetich, Ilaria, et al., "Hyaluronic Acid in Cutaneous Intrinsic Aging," International Journal of Dermatology, vol. 33, N . 2, Feb. 1994.

(Continued)

*Primary Examiner* — Ekaterina Poliakova-Georgantas
(74) *Attorney, Agent, or Firm* — Ice Miller LLP

(57) ABSTRACT

The present invention relates to compositions of small activating nucleic acid molecules for increasing the expression of HMBS gene and a use thereof. The small activating nucleic acid molecule can be a double-stranded or single-stranded RNA molecule targeting the promoter region of the HMBS gene. The first nucleic acid strand and the second nucleic acid strand each contain a complementary region, and the complementary regions can form a double-stranded nucleic acid structure, which can promote the expression of the HMBS gene. The first nucleic acid strand or the second nucleic acid strand independently have a length of 16 to 35 nucleotides. The 3' terminus of the two oligonucleotide strands may have an overhang of 0 to 6 nucleotides in length. The small activating nucleic acid molecule for the HMBS gene can be used to up-regulate mRNA and protein expressions of the HMBS gene in a cell and promote enzymatic activity thereof

19 Claims, 8 Drawing Sheets
Specification includes a Sequence Listing.

(56) References Cited

FOREIGN PATENT DOCUMENTS

| JP | 2013532973 | | 8/2013 | |
|----|-----------|----|--------|----|
| WO | 9629411 | | 9/1996 | |
| WO | WO-2005014811 | A2 * | 2/2005 | ......... A61K 49/0008 |
| WO | 2006005042 | | 1/2006 | |
| WO | 2008095357 | A1 | 8/2008 | |
| WO | 2009100438 | | 8/2009 | |
| WO | 2010144740 | | 12/2010 | |
| WO | 2011150005 | | 12/2011 | |
| WO | 2011161460 | | 12/2011 | |
| WO | 2012046085 | A2 | 4/2012 | |
| WO | 2013173638 | | 11/2013 | |
| WO | 2013173652 | | 11/2013 | |
| WO | 2015051283 | | 4/2015 | |
| WO | 2015162422 | A1 | 10/2015 | |
| WO | 2016077689 | A1 | 5/2016 | |
| WO | 2016145608 | | 9/2016 | |
| WO | 2016145608 | A1 | 9/2016 | |
| WO | 2016170348 | A2 | 10/2016 | |
| WO | 2016170349 | | 10/2016 | |
| WO | 2017087486 | A1 | 5/2017 | |
| WO | 2017106283 | | 6/2017 | |
| WO | 2017218884 | | 12/2017 | |
| WO | 2018017991 | A1 | 1/2018 | |
| WO | 2019196887 | | 10/2019 | |
| WO | 2020135677 | | 7/2020 | |
| WO | 2020151726 | | 7/2020 | |
| WO | 2020155534 | | 8/2020 | |
| WO | 2021000928 | | 1/2021 | |
| WO | 2021052470 | | 3/2021 | |

OTHER PUBLICATIONS

Gong Hua, et al., "Construction of dsRNA Expression Vector and Research of RNA Activation", Journal of Contemporary Urologic and Reproductive Oncology, (Oct. 22, 2011), vol. 3, No. 5, ISSN 1674-4624.

Harper et al., The p21 Cdk-interacting protein Cip1 is a potent inhibitor of G1 cyclin-dependent kinases, vol. 75, No. 4, pp. 805-816 (1993).

Harrington et al., "Gene Therapy for Prostate Cancer: Current Status and Future Prospects," J Urol, vol. 166, pp. 1220-1233 (2001).

Hindupur, S. K., et al., "The protein histidine phosphatase LHPP is a tumour suppressor," Nature, vol. 7698, No. 555, Mar. 29, 2018.

Huang et al., "RNAa Is Conserved in Mammalian Cells," PLoS One, vol. 5, Iss. 1, pp. e8848 (2010).

Huang et al., "Upregulation of Cyclin B1 by miRNA and its implications in cancer," Nucleic Acids Res, vol. 40, No. 4, pp. 1695-1707 (2012).

International Search Report issued Jun. 28, 2019 in International Application No. PCT/CN2019/082149, 8 pages.

International Search Report issued Mar. 27, 2020 in PCT/CN2019/129025, 12 pages.

International Search Report issued Nov. 4, 2019 in PCT/CN2019/092720.

International Search Report issued Apr. 24, 2020 in corresponding PCT/CN2020/073663.

International Search Report issued Oct. 10, 2020 in corresponding PCT/CN2020/100093.

Janowski et al., "Activating gene expression in mammalian cells with promoter-targeted duplex RNAs," Nat Chem Biol, vol. 3, No. 3, pp. 166-173 (2007).

Jiao et al., "RNA-mediated gene activation," Epigenetics, vol. 9, Iss. 1, pp. 27-36 (2014).

Kang et al. (Cancer Res., 2012, 72(19), 5069-5079).

Karlsson, Thommie, et al., "Water fluxes through aquaporin-9 prime epithelial cells for rapid wound healing," Biochemical and Biophysical Research Communications, No. YBBRC 29690, Dec. 22, 2012.

Kosaka et al., "Targeted p21 WAF1/CIP1 Activation by RNAa Inhibits Hepatocellular Carcinoma Cells," Nucleic Acid Therapeutics, vol. 22, No. 5, pp. 335-343 (2012).

Li, "Small RNA-Guided Transcriptional Gene Activation (RNAa) in Mammalian Cells," RNA Activation, Advances in Experimental Medicine and Biology, vol. 983, Ch. 1, pp. 1-20 (2017).

Li, L.C, et al, "Small dsRNAs Induce Transcriptional Activation in Human Cells," PNAS, vol. 103, No. 46, pp. 17337-17342, Nov. 14, 2006.

Longas, Maria O., et al., "Evidence for Structural Changes in Dermatan Sulfate and Hyaluronic Acid with Aging," Carbohydrate Research, vol. 159, pp. 127-136, 1987.

Place et al., "MicroRNA-373 induces expression of genes with complementary promoter sequences," Proc Natl Acad Sci USA, vol. 105, No. 5, pp. 1608-1613 (2008).

Schrader, A., et al., "Effects of Glyceryl Glucoside on AQP3 Expression, Barrier Function and Hydration of Human Skin," Skin Pharmacology and Physiology, vol. 25, pp. 192-199, May 15, 2012.

Seth et al., The C. elegans CSR-1 Argonaute Pathway Counteracts Epigenetic Silencing to Promote Germline Gene Expression, Developmental Cell, vol. 27, pp. 656-663 (2013).

Turner et al., "Autoregulation of lin-4 microRNA transcription by RNA activatio (RNAa) in C. elegans," Cell Cycle 13:5, 772-781; Mar. 1, 2014.

Woo, et al., "Gene activation of SMN by selective disruption of lncRNA-mediated recruitment of PRC2 for the treatment of spinal muscular atrophy," Proceedings of the National Academy of Sciences, Feb. 21, 2017 National Academy of Sciences, US, vol. 114, Nr: 8, pp. E1509-E1518, Feb. 13, 2017.

Written Opinion issued Apr. 24, 2020 in corresponding PCT/CN2020/073663.

Wu et al., "Roles of the Tumor Suppressor p53 and the Cycl in-dependent Kinase Inhibitor p21 WAF1/CIP1 in Receptor-mediated Apoptosis of WEHI231 B Lymphoma Cells," J Exp Med, vol. 187, No. 10, pp. 1671-1679 (1998).

Yang et al. (Cancer Letters, 265, 2008, 206-214).

Zheng, Jiangli, et al., "Down-regulation of LHPP in cervical cancer influences cell proliferation, metastasis and apoptosis by modulating AKT," Biochemical and Biophysical Research Communications, vol. 503, No. 2, Aug. 2, 2018.

Wijayadi, L.Y., et al., "Asiaticoside increases aquaporin-3 protein expression in the cytoplasm of normal human epidermal keratinocytes," Universa Medicina, vol. 36, No. 1, pp. 25-33, Apr. 7, 2017, Abstract.

Zeng, Xin, et al., "Screen for modulators of atonal homolog 1 gene expression using notch pathway-relevant gene transcription based cellular assays," PLOS ONE, vol. 13, No. 12, pp. 1-16, Dec. 12, 2018.

Database EMBL (Online), "JP 2016533752-A/494826: Oligonucleotide Probes and Uses Thereof," XP002809531, retrieved from EBI accession No. EM_PAT:LV449428, Database accession No. LV449428, Mar. 31, 20217, one page.

Database Geneseq (Online), "Viral regulatory MiRNA Seq ID No. 175961," XP002809532, retrieved from EBI accession No. GSN:AJJ23641, Database accession No. AJJ23641, Dec. 28, 2007, one page.

Zhang, Yong-Li, et al., "Small activating RNA activation of ATOH1 promotes regeneration of human inner ear hair cells," Bioengineered, vol. 13, No. 3, pp. 6729-6739, Mar. 1, 2022.

Koonin et al. Chapter 2 Evolutionary Concept in Genetics and Genomics, Sequence—Evolution—Function: Computational Approaches in Comparative Genomics. Boston: Kluwer Academic; 2003; NCBI Bookshelf (Year: 2003), 25 pages.

Webber et al., Genes and homology, Current Biology, vol. 14(9): R:332-R333 (May 4, 2004) (Year: 2004).

Rost, Twilight zone of protein sequence alignments, Protein Engineering, vol. 12(2): 85-94 (1999) (Year: 1999).

Kuter, David J., "Thrombopoietin and Thrombopoietin Mimetics in the Treatment of Thrombocytopenia," Annual Review of Medicine, 60:1, 193-206, Feb. 1, 2009.

Kwok, Albert, et al, "Developing small activating RNA as a therapeutic: current challenges and promises," Ther Deliv. 2019, vol. 10(3), pp. 151-164.

Wang, Ji, et al, "Inducing gene expression by targeting promoter sequences using small activating RNAs," J Biol Methods, 2015, vol. 2(1), 25 pages.

(56)                              References Cited

OTHER PUBLICATIONS

Voutila, J., et al, "Development and Mechanism of Small Activating RNA Targeting CEBPA, a Novel Therapeutic in Clinical Trials for Liver Cancer," Molecular Therapy, 2017, vol. 25(12), pp. 2705-2714.
D'Avola, D., et al., "Phase I open label liver-directed gene therapy clinical trial for actute intermittent porphyria," Journal of Hepatology, 65:4, 776-783 (2016).
Jiang Lei et al, "Systemic messenger RNA as an etiological treatment for actue intermittent porphyria," Nature Medicine, 24:12, 1899-1909 (2018).
Meng, Xing, et al., "Small activating RNA bind to the genomic target site in a seed-region-dependent manner," Nucleic Acids Research, vol. 44, No. 5, pp. 2274-2282, Feb. 11, 2016.
European Search Report issued Nov. 30, 2022.
Extended European Search Report issued Dec. 12, 2022.
Kuter, David J. "Thrombopoietin and Thrombopoietin Mimetics in the Treatment of Thrombocytopenia," Annual Review of Medicine, vol. 60, No. 1, pp. 193-206, Feb. 1, 2009.
Vaschetto, Luis Maria, "RNA Activation: A Diamond in the Rough for Genome Engineers," Journal of Cellular Biochemistry, Vo. 119, No. 1, pp. 247-249, Jul. 17, 2017.
International Search Report mailed Aug. 5, 2020 in PCT/CN2020/087844.
Written Opinion mailed Aug. 5, 2020 in PCT/CN2020/087844.

* cited by examiner

A

B

C

A

B

SEQUENCE LISTING

<160> NUMBER OF SEQ ID NOS: 69

<210> SEQ ID NO 1
<211> LENGTH: 45
<212> TYPE: DNA
<213> ORGANISM: Artificial Sequence
<220> FEATURE:
<223> OTHER INFORMATION: Synthetic DNA Construct

<400> SEQUENCE: 1
tagcctgggc aacatagtga ggccacctcc ccgctgtctc tataa          45

<210> SEQ ID NO 2
<211> LENGTH: 179
<212> TYPE: DNA
<213> ORGANISM: Artificial Sequence
<220> FEATURE:
<223> OTHER INFORMATION: Synthetic DNA Construct

<400> SEQUENCE: 2
tgctgcctat ttcaaggttg tagcaaagct aagtttgaac agagcaaagg aagcgccata          60
gaagctgcac tacttgctca tgtcacagct ggggaatggg gtggtcgaat ggggaggtcc          120
actgtcgcaa tgttccaatt cccgcccaga gggagggacc tccccttcga gggagggcg          179

<210> SEQ ID NO 3

-continued

```
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 3
ccuguuuacc aaggagcuut t                                                     21

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 4
aagcuccuug guaaacaggt t                                                     21

<210> SEQ ID NO 5
<211> LENGTH: 21
<212> TYPE: DNA
<213> ORGANISM: Artificial Sequence
<220> FEATURE:
<223> OTHER INFORMATION: Primer Sequence

<400> SEQUENCE: 5
acagctatga aggatgggca a                                                     21

<210> SEQ ID NO 6
<211> LENGTH: 20
<212> TYPE: DNA
<213> ORGANISM: Artificial Sequence
<220> FEATURE:
<223> OTHER INFORMATION: Primer Sequence

<400> SEQUENCE: 6
atcttcatgc tgggcaggga                                                       20

<210> SEQ ID NO 7
<211> LENGTH: 21
<212> TYPE: DNA
<213> ORGANISM: Artificial Sequence
<220> FEATURE:
<223> OTHER INFORMATION: Primer Sequence

<400> SEQUENCE: 7
atggacagga ctgaacgtct t                                                     21

<210> SEQ ID NO 8
<211> LENGTH: 20
<212> TYPE: DNA
<213> ORGANISM: Artificial Sequence
<220> FEATURE:
<223> OTHER INFORMATION: Primer Sequence

<400> SEQUENCE: 8
tccagcaggt cagcaaagaa                                                       20

<210> SEQ ID NO 9
<211> LENGTH: 20
<212> TYPE: DNA
<213> ORGANISM: Artificial Sequence
<220> FEATURE:
<223> OTHER INFORMATION: Primer Sequence

<400> SEQUENCE: 9
```
ataatcccaa gcggtttgct                                                        20

<210> SEQ ID NO 10
<211> LENGTH: 20
<212> TYPE: DNA
<213> ORGANISM: Artificial Sequence
<220> FEATURE:
<223> OTHER INFORMATION: Primer Sequence

<400> SEQUENCE: 10
ctgccagtct ggactgttct                                                        20

<210> SEQ ID NO 11
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 11
ccatagaagc tgcactact                                                         19

<210> SEQ ID NO 12
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 12
cgccatagaa gctgcacta                                                         19

<210> SEQ ID NO 13
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 13
catagtgagg ccacctccc                                                         19

<210> SEQ ID NO 14
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 14
ccacctcccc gctgtctct                                                         19

<210> SEQ ID NO 15
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 15
tgctgcctat ttcaaggtt                                                         19

<210> SEQ ID NO 16
<211> LENGTH: 19
<212> TYPE: DNA

<213> ORGANISM: Artificial Sequence
<220> FEATURE:
<223> OTHER INFORMATION: Functional Target Sequence

<400> SEQUENCE: 16
cctccccttc gagggaggg                                              19

<210> SEQ ID NO 17
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 17
agagggaggg acctcccct                                              19

<210> SEQ ID NO 18
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 18
ctccccttcg agggagggc                                              19

<210> SEQ ID NO 19
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 19
caacatagtg aggccacct                                              19

<210> SEQ ID NO 20
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 20
gccacctccc cgctgtctc                                              19

<210> SEQ ID NO 21
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 21
ctggggaatg gggtggtcg                                              19

<210> SEQ ID NO 22
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 22
tcaaggttgt agcaaagct                                              19

-continued

```
<210> SEQ ID NO 23
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 23
gtggtcgaat ggggaggtc                                              19

<210> SEQ ID NO 24
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 24
acctccccgc tgtctctat                                              19

<210> SEQ ID NO 25
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 25
agctaagttt gaacagagc                                              19

<210> SEQ ID NO 26
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 26
atagtgaggc cacctcccc                                              19

<210> SEQ ID NO 27
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 27
tcacagctgg ggaatgggg                                              19

<210> SEQ ID NO 28
<211> LENGTH: 19
<212> TYPE: DNA
<213> ORGANISM: Artificial Sequence
<220> FEATURE:
<223> OTHER INFORMATION: Functional Target Sequence

<400> SEQUENCE: 28
gggaatgggg tggtcgaat                                              19

<210> SEQ ID NO 29
<211> LENGTH: 19
<212> TYPE: DNA
<213> ORGANISM: Artificial Sequence
<220> FEATURE:
```

-continued

<223> OTHER INFORMATION: Functional Target Sequence

<400> SEQUENCE: 29
gccatagaag ctgcactac                                            19

<210> SEQ ID NO 30
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 30
ccauagaagc ugcacuacut t                                         21

<210> SEQ ID NO 31
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 31
cgccauagaa gcugcacuat t                                         21

<210> SEQ ID NO 32
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 32
cauagugagg ccaccuccct t                                         21

<210> SEQ ID NO 33
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 33
ccaccucccc gcugucucut t                                         21

<210> SEQ ID NO 34
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 34
ugcugccuau uucaagguut t                                         21

<210> SEQ ID NO 35
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 35 ccucccuuc gagggagggt t                                          21

-continued

```
<210> SEQ ID NO 36
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 36
agagggaggg accuccccut t                                                21

<210> SEQ ID NO 37
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 37
cuccccuucg agggagggct t                                                21

<210> SEQ ID NO 38
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 38
caacauagug aggccaccut t                                                21

<210> SEQ ID NO 39
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 39
gccaccuccc cgcugucuct t                                                21

<210> SEQ ID NO 40
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 40
cuggggaaug ggguggucgt t                                                21

<210> SEQ ID NO 41
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 41
ucaagguugu agcaaagcut t                                                21

<210> SEQ ID NO 42
<211> LENGTH: 21
<212> TYPE: DNA
<213> ORGANISM: Artificial Sequence
<220> FEATURE:
<223> OTHER INFORMATION: Synthetic DNA/RNA Construct
```

-continued

<400> SEQUENCE: 42
guggucgaau ggggagguct t                                           21

<210> SEQ ID NO 43
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 43
accuccccgc ugucucuaut t                                           21

<210> SEQ ID NO 44
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 44
agcuaaguuu gaacagagct t                                           21

<210> SEQ ID NO 45
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 45
auagugaggc caccuccct t                                            21

<210> SEQ ID NO 46
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 46
ucacagcugg ggaauggggt t                                           21

<210> SEQ ID NO 47
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 47
gggaaugggg uggucgaaut t                                           21

<210> SEQ ID NO 48
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 48
gccauagaag cugcacuact t                                           21

<210> SEQ ID NO 49
<211> LENGTH: 21

```
<212> TYPE: DNA
<213> ORGANISM: Artificial Sequence
<220> FEATURE:
<223> OTHER INFORMATION: Synthetic DNA/RNA Construct

<400> SEQUENCE: 49
aguagugcag cuucuauggt t                                                 21

<210> SEQ ID NO 50
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 50
uagugcagcu ucuauggcgt t                                                 21

<210> SEQ ID NO 51
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 51
gggagguggc cucacuaugt t                                                 21

<210> SEQ ID NO 52
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 52
agagacagcg gggagguggt t                                                 21

<210> SEQ ID NO 53
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 53
aaccuugaaa uaggcagcat t                                                 21

<210> SEQ ID NO 54
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 54
cccucccucg aaggggaggt t                                                 21

<210> SEQ ID NO 55
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 55
```

-continued aggggagguc ccucccucut t                                                            21

<210> SEQ ID NO 56
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 56
gcccucccuc gaaggggagt t                                                            21

<210> SEQ ID NO 57
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 57
agguggccuc acuauguugt t                                                            21

<210> SEQ ID NO 58
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 58
gagacagcgg ggagguggct t                                                            21

<210> SEQ ID NO 59
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 59
cgaccacccc auuccccagt t                                                            21

<210> SEQ ID NO 60
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 60
agcuuugcua caaccuugat t                                                            21

<210> SEQ ID NO 61
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 61
gaccucccca uucgaccact t                                                            21

<210> SEQ ID NO 62
<211> LENGTH: 21
<212> TYPE: DNA
<213> ORGANISM: Artificial Sequence -continued

```
<220> FEATURE:
<223> OTHER INFORMATION: Synthetic DNA/RNA Construct

<400> SEQUENCE: 62
auagagacag cggggaggut t                                          21

<210> SEQ ID NO 63
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 63
gcucuguuca aacuuagcut t                                          21

<210> SEQ ID NO 64
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 64
ggggaggugg ccucacuaut t                                          21

<210> SEQ ID NO 65
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 65
ccccauuccc cagcugugat t                                          21

<210> SEQ ID NO 66
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 66
auucgaccac cccauuccct t                                          21

<210> SEQ ID NO 67
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 67
guagugcagc uucuauggct t                                          21

<210> SEQ ID NO 68
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 68
acuacugagu gacaguagat t                                          21
```

-continued

```
<210> SEQ ID NO 69
<211> LENGTH: 21
<212> TYPE: DNA
<213> ORGANISM: Artificial Sequence
<220> FEATURE:
<223> OTHER INFORMATION: Synthetic DNA/RNA Construct

<400> SEQUENCE: 69
ucuacuguca cucaguagut t                                                        21
```

OLIGOMERIC NUCLEIC ACID MOLECULE, AND APPLICATION THEREOF IN AN ACUTE INTERMITTENT PORPHYRIA TREATMENT

CROSS-REFERENCE TO RELATED APPLICATION

This application is a Section 371 of International Application No. PCT/CN2020/087844 filed Apr. 29, 2020, which was published in the Chinese language Nov. 5, 2020, under International Publication No. WO 2020/221309 A1, which claims priority to Chinese Patent Application No. 201910364093.9 filed Apr. 30, 2019, the disclosures of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name of "065786.11048-6US1 sequence listing.txt" and a creation date of Jan. 5, 2022, and having a size of 13.8 kb. The sequence listing submitted via EFS-Web is part of the specification and is herein incorporated by reference in its entirety.

TECHNICAL FIELD

The present invention relates to the technical field of nucleic acids, specifically as it relates to an oligomeric nucleic acid molecule related to gene activation, e.g, a small activating nucleic acid molecule and a use thereof in activating/upregulating the expression of the hydroxymethylbilane synthase HMBS gene and uses thereof in treating diseases, e.g., acute intermittent porphyria, caused by insufficient expression or decreased activity of HMBS.

BACKGROUND

Hereditary proporphyrias are a series of diseases caused by the lack of activity of specific enzymes in the heme biosynthesis pathway, also referred to as a porphyrin pathway. The lack of enzymes in the porphyrin pathway leads to the insufficient production of heme and the accumulation of porphyrin precursors and porphyrin, while a high tissue concentrations of porphyrin precursors and porphyrin results in tissue toxicity.

Among hereditary porphyrias, acute intermittent porphyria (AIP). e.g., autosomal dominant hereditary AIP, variegate porphyria (VP), e.g, autosomal dominant hereditary VP, hereditary coproporphyria, chromaffin cells or HCP, e.g., autosomal dominant HCP, and 5'-aminolevulinic acid, also referred to as δ-aminolevulinic acid or ALA, dehydratase deficiency porphyria (ADP), e.g., autosomal recessive ADP, are classified as acute hepatic porphyria, which are manifested as life-threatening acute nervous system symptoms involving the autonomic nerves, the peripheral nerves, and the central nervous system, comprising severe abdominal pain, hypertension, tachycardia, constipation, motor weak, paralysis, and epilepsy. Improper treatment may result in quadriplegia, respiratory disorder, and even death. Many drugs capable of inducing cytochrome P450, dieting, changes in the hormone levels may induce the acute attack of porphyrias by increasing the activity of hepatic 5'-aminolevulinic acid synthetase 1 (ALAS1) (Balwani and Desnick, *Blood,* 120: 4496-4504, 2012).

The most common acute hepatic porphyria, AIP, also referred to as porphobinogen deaminase (PBGD) deficiency or hydroxymethylbilane synthase (HMBS) deficiency, is an autosomal dominant hereditary disease caused by an HMBS gene mutation, has an incidence rate between 5 to 10 persons per population of 100,000, of which about 5% to 10% of patients have symptoms. One allele of HMBS gene is mutated in an AIP patient, which causes the protein expression of hydroxymethylbilane synthase to be reduced in half (haploinsufficiency) resulting in low enzymatic activity, leading to the in vivo accumulation of ALA and porphobilinogen (PBG), and insufficient heme synthesis.

Intravenous injection of hemin is usually intended for treatment and prevention during an acute attack of AIP in a patient. Hemin provides exogenous heme to inhibit the negative feedback of ALAS1, thereby reducing the production of ALA and PBG. Although the responses of patients are good, the therapeutic effect of hemin is slow, usually taking 2 to 4 days or longer to achieve normal urinary PBG and ALA concentrations. Due to the rapid metabolism of hemin, three to four intraveneous injections are usually required to effectively treat or prevent acute attack. Additionally, repeated injections may lead to iron overload and phlebitis. At present, the only curative therapy is liver transplantation. However, there are significant complications with liver transplantation, mortality, and liver sourcing is limited.

In view of the limitations of these current therapeutic methods, alternative therapeutic methods which are more effective, lasting, rapid, and safer are needed.

The present invention provides a method which utilizes a small activating RNA (saRNA) to specifically activate the HMBS gene expression levels in vivo, stimulating cells to produce endogenous porphobilinogen deaminase, also referred to as hydroxymethylbilane synthase, to restore its normal level in the cells, so that AIP can be effectively treated.

SUMMARY

The present invention provides a small activating nucleic acid molecule (saRNA), which treats diseases, e.g., acute intermittent porphyria, caused by the insufficient expression or decreased activity of HMBS by activating/upregulating HMBS gene transcription to increase HMBS protein expression.

In one aspect of the present invention, a small activating nucleic acid molecule is provided, which can activate or up-regulate the expression of HMBS gene in a cell. One strand of the small activating nucleic acid molecule of the present invention has at least more than 75% homology or complementarity to a sequence of 16 to 35 nucleotides in length in the promoter region of HMBS gene, thereby enabling the activation or up-regulation of the gene expression, wherein the promoter region comprises 400 base pairs (bp) of nucleotide sequence upstream of the transcription start site of HMBS gene. Specifically, one strand of the small activating nucleic acid molecule of the present invention comprises a nucleotide sequence having at least more than 75% homology or complementarity to any continuous sequence of 16 to 35 nucleotides in length in the promoter region of HMBS gene, wherein the promoter region comprises 400 bp of nucleotides upstream of the transcription start site of HMBS gene. In one specific embodiment, one strand of the small activating nucleic acid molecule of the present invention comprises or is selected from a nucleotide sequence having at least 75% (e.g., at least about 79%, about 80%, about 85%, about 90%, about 95%, about 99% or 100%) homology or complementarity to 16 to 35 continuous nucleotides in a region (region 1) from −395 bp to −351 bp (tagcctgggcaacatagtgaggccacctccccgctgtctctataa, SEQ ID NO: 1) and a region (region 2) from −179 bp to −1 bp (tgctgcctatttcaaggttgtagcaaagctaagttt-gaacagagcaaaggaagcgccatagaagctgcactacttgctcatgt-cacagctgggg aatggggtggtcgaatgggagggtccactgtcgcaatgttc-caattcccgcccagagggagggacctccccttcgagggagggcg, SEQ ID NO: 2) upstream of the promoter of HMBS gene. More specifically, in one embodiment, one strand of the small activating nucleic acid molecule of the present invention has at least 75%, e.g., at least about 79%, about 80%, about 85%, about 90%, about 95% or about 99% homology or complementarity to any continuous sequence of 16 to 35 nucleotides in length selected from SEQ ID NO: 1 and SEQ ID NO: 2. In one specific embodiment, one strand of the small activating nucleic acid molecule of the present invention comprises or is selected from a nucleotide sequence having at least 75% e.g., at least about 79%, about 80%, about 85%, about 90%, about 95%, about 99% or 100% homology or complementarity to any continuous sequence of 16 to 35 nucleotides in length selected from SEQ ID NO: 1 and SEQ ID NO: 2. In a more specific embodiment, one strand of the small activating nucleic acid molecule of the present invention consists of a nucleotide sequence which has at least 75%, e.g., at least about 79%, about 80%, about 85%, about 90%, about 95%, about 99% or 100% homology or complementarity to any continuous sequence of 16 to 35 nucleotides in length selected from SEQ ID NO: 1 and SEQ ID NO: 2.

In the present invention, the small activating nucleic acid molecule of the present invention comprises a double-stranded small activating nucleic acid molecule targeting promoter region of HMBS gene, comprising a first nucleic acid strand and a second nucleic acid strand, wherein the first nucleic acid strand has at least 75% homology or complementarity to any continuous sequence of 16 to 35 nucleotides in length in SEQ ID NO. 1 or SEQ ID NO. 2 in the promoter of HMBS gene, the second nucleic acid strand has at least 75% complementarity to the first nucleic acid strand, and the first nucleic acid strand and the second nucleic acid strand can complementarily form a double-stranded nucleic acid structure between the two fragments, capable of activating the expression of HMBS gene in a cell.

The sense nucleic acid strand and antisense nucleic acid strand of the small activating nucleic acid molecule of the present invention can be present either on two different nucleic acid strands or on the same nucleic acid strand. When the sense nucleic acid strand and the antisense nucleic acid strand are located on two different strands, at least one strand of the small activating nucleic acid molecule may have an overhang at any of 5' terminus and 3' terminus, e.g., an overhang of 0 to 6 nucleotides in length at the 3' terminus. Preferably, both strands of the small activating nucleic acid molecule of the present invention have overhangs, and more preferably, the 3' terminus of both strands of the small activating nucleic acid molecule may have overhangs of 0 to 6 nucleotides in length, most preferably overhangs of 2 or 3 nucleotides in length. Preferably, the nucleotide of the overhang can be dT or U, or the overhang can be a natural nucleotide overhang. The natural nucleotide overhang described in the present invention means that nucleotides protruding from the terminus of the sense nucleic acid fragment or the antisense nucleic acid fragment are identical or complementary to the nucleotides of a corresponding target sequence.

The small activating nucleic acid molecule may also comprise a single-stranded RNA molecule capable of forming a double-stranded region hairpin structure. In one embodiment, the small activating nucleic acid molecule of the present invention is a single-stranded RNA molecule targeting promoter region of HMBS gene, wherein the small activating nucleic acid molecule can form a double-stranded region hairpin structure. When the sense nucleic acid strand and the antisense nucleic acid strand are present on the same nucleic acid strand, preferably, the small activating nucleic acid molecule can be a hairpin single-stranded nucleic acid molecule, wherein the complementary regions of the sense nucleic acid fragment and the antisense nucleic acid fragment form a double-stranded nucleic acid structure between the two fragments, which can induce the expression of HMBS gene in a cell through, for example, an RNA activation mechanism.

In the aforementioned small activating nucleic acid molecule, the sense nucleic acid fragment and the antisense nucleic acid fragment may have 16 to 35 nucleotides (e.g., 16, 17, 18, 19, 20, 21, 22, 23, 24, 25, 26, 27, 28, 29, 30, 31, 32, 33, 34 or 35 nucleotides) in length.

In one embodiment, the sense strand of the small activating nucleic acid molecule of the present invention has at least 75% e.g., at least about 79%, about 80%, about 85%, about 90%, about 95%, about 99% or 100% identity or homology to any nucleotide sequence selected from SEQ ID NOs: 30-48, and antisense strand thereof has at least 75%, e.g., at least about 79%, about 80%, about 85%, about 90%, about 95%, about 99% or 100% identity or homology to any nucleotide sequence selected from SEQ ID NOs: 49-67. In one embodiment, the sense strand of the small activating nucleic acid molecule of the present invention comprises or is selected from a sequence having at least 75%, e.g., at least about 79%, about 80%, about 85%, about 90%, about 95%, about 99% or 100% identity or homology to any nucleotide sequence selected from SEQ ID NOs: 30-48, and antisense strand thereof comprises or is selected from a sequence having at least 75%, e.g., at least about 79%, about 80%, about 85%, about 90%, about 95%, about 99% or 100% identity or homology to any nucleotide sequence selected from SEQ ID NOs: 49-67. In one embodiment, the sense strand of the small activating nucleic acid molecule of the present invention consists of a sequence having at least 75%, e.g., at least about 79%, about 80%, about 85%, about 90%, about 95%, about 99% or 100% identity or homology to any nucleotide sequence selected from SEQ ID NOs: 30-48, and antisense strand thereof consists of a sequence having at least 75%, e.g., at least about 79%, about 80%, about 85%, about 90%, about 95%, about 99% or 100%) identity or homology to any nucleotide sequence selected from SEQ ID NOs: 49-67. In a specific embodiment, the sense strand of the small activating nucleic acid molecule of the present invention can be a sequence shown as any nucleotide sequence selected from SEQ ID NOs: 30-48, and antisense strand thereof can be a sequence shown as any nucleotide sequence selected from SEQ ID NOs: 49-67.

In one embodiment, the small activating nucleic acid molecule described herein can be synthesized, transcribed in vitro or expressed by a vector.

All the nucleotides in the small activating nucleic acid molecule described herein can be natural non-chemically modified nucleotides or may comprise at least one modification. In one embodiment, the modification in the small activating nucleic acid molecule described herein can be chemical modification, for example, at least one nucleotide is a chemical modification. The chemical modification used in the present invention may comprise or be selected from one or more or any combination of the following modifications:

(1) modification of a phosphodiester bond of nucleotides in the nucleotide sequence of the small activating nucleic acid molecule;

(2) modification of 2'-OH of the ribose in the nucleotide sequence of the small activating nucleic acid molecule; and (3) modification of a base in the nucleotide of the small activating nucleic acid molecule;

(4) at least one nucleotide in the nucleotide sequence of the small activating nucleic acid molecule being a locked nucleic acid.

The chemical modification described herein is well-known to those skilled in the art, and the modification of the phosphodiester bond refers to the modification of oxygen in the phosphodiester bond, including but not limited to phosphorothioate modification and boranophosphate modification. Both modifications can stabilize a small activating nucleic acid molecule structure and maintain high specificity and high affinity for base pairing.

The ribose modification refers to the modification of 2'-OH in pentose of a nucleotide, i.e., the introduction of certain substituents into hydroxyl positions of the ribose, for example, including but not limited to 2'-fluoro modification, 2'-oxymethyl modification, 2'-oxyethylidene methoxy modification, 2,4'-dinitrophenol modification, locked nucleic acid (LNA), 2'-amino modification, 2'-deoxy modification.

The base modification refers to the modification of the base of a nucleotide, for example, including but not limited to 5'-bromouracil modification, 5'-iodouracil modification, N-methyluracil modification, 2,6-diaminopurine modification.

These modifications can increase the bioavailability of the small activating nucleic acid molecule, improve affinity to a target sequence and enhance resistance to nuclease hydrolysis in a cell.

In addition, in order to promote cellular uptake of the small activating nucleic acid , on the basis of the aforementioned modifications, a lipophilic group, such as cholesterol, can be conjugated onto the terminus of the sense strand or antisense strand of the small activating nucleic acid molecule to facilitate transmembrane trafficking across the lipid bi-layer cell membrane and nuclear envelope to finally bind with its gene promoter target in the cell nucleus.

After contacting a cell, the small activating nucleic acid molecule provided by the present invention can effectively activate or upregulate the expression of HMBS gene in the cell, preferably upregulate the expression by at least 10%.

Another aspect of the present invention also relates to a nucleic acid coding the small activating nucleic acid molecule described herein. In one embodiment, the nucleic acid may be a DNA molecule.

Another aspect of the present invention provides a cell comprising the aforementioned small activating nucleic acid molecule or the nucleic acid coding the small activating nucleic acid molecule described herein. In one embodiment, the small activating nucleic acid molecule of the present invention can be a double-stranded small activating nucleic acid molecule targeting the promoter region of HMBS gene, which comprises a sense strand and an antisense strand. In another embodiment, the small activating nucleic acid molecule of the present invention can be a single-stranded nucleic acid molecule coding the small activating nucleic acid molecule targeting the promoter region of HMBS gene.

Another aspect of the present invention provides a kit comprising the aforementioned small activating nucleic acid molecule and the nucleic acid coding the small activating nucleic acid molecule described herein.

Another aspect of the present invention relates to a use of the aforementioned small activating nucleic acid molecule and the nucleic acid coding the small activating nucleic acid molecule described herein in preparing a drug for activating/up-regulating the expression of HMBS gene in a cell.

Another aspect of the present invention relates to a use of the aforementioned small activating nucleic acid molecule, the nucleic acid coding the small activating nucleic acid molecule described herein and the cell of the present invention in preparing a drug for treating a disease caused by insufficient expression or decreased activity of HMBS in a subject. In one embodiments, the disease caused by insufficient expression or decreased activity of HMBS may comprise hereditary porphyrias. Hereditary porphyrias may comprise, for example, acute intermittent porphyria.

Another aspect of the present invention relates to a use of the aforementioned small activating nucleic acid molecule, the nucleic acid coding the small activating nucleic acid molecule described herein and the cell of the present invention in preparing a drug for treating acute intermittent porphyria in a subject.

Another aspect of the present invention also relates to a method for treating a disease caused by insufficient expression or decreased activity of HMBS in a subject, which comprises administering the aforementioned small activating nucleic acid molecule, the nucleic acid coding the small activating nucleic acid molecule described herein or the cell of the present invention to a subject.

Another aspect of the present invention also relates to a method for treating acute intermittent porphyria in a subject, which comprises administering the aforementioned small activating nucleic acid molecule, the nucleic acid coding the small activating nucleic acid molecule described herein or the cell of the present invention to a subject.

The present invention also relates to a method for activating/upregulating the expression of HMBS gene in a cell. The method comprises administering the aforementioned small activating nucleic acid molecule or the nucleic acid coding the small activating nucleic acid molecule described herein to a cell.

The small activating nucleic acid molecule of the present invention can be directly introduced into a cell, or can be produced in the cell after a nucleotide sequence coding the small activating nucleic acid molecule is introduced into a cell. The cell is preferably a mammalian cell, more preferably a human cell. The aforementioned cell can be in vitro, such as a cell line or a cell strain, or can be isolated from a mammalian body, such as a human body. The human body is a patient suffering from a disease or symptom caused by decreased protein expression of HMBS. The small activating nucleic acid molecule described herein can be administered at a sufficient dose to treat a symptom caused by decreased protein expression of HMBS. Specifically, the symptom caused by the lack of HMBS protein expression is acute intermittent porphyria.

Another aspect of the present invention provides an isolated target site of small activating nucleic acid molecule on HMBS gene, wherein the target site is a continuous sequence having a length of 16 to 35 nucleotides in the promoter region of HMBS gene, and preferably, the target site is any continuous sequence of 16 to 35 nucleotides in length in any of sequences set forth in SEQ ID NOs: 1-2. Specifically, the target site comprises or is selected from any or the nucleotide sequence selected from SEQ ID Nos: 11-29.

Advantages of the Present Invention

The small activating nucleic acid molecule capable of activating/upregulating the expression of HMBS gene provided by the present invention can permanently activate HMBS gene, therefore efficiently and specifically upregulate or restore the expression of HMBS gene and HMBS protein and the activity of the enzyme with lower toxic and side effects, and can be used in preparing a drug or formulation for activating / upregulating the expression of HMBS gene and HMBS protein in a cell.

BRIEF DESCRIPTION OF THE DRAWINGS

FIG. 4 shows small activating RNAs (saRNAs) candidates activating HMBS mRNA expression of in different liver cells. The saRNAs (n=13, final concentration: 20 nM) shown were used to transfect the human hepatocellular carcinoma cells (Huh7)

FIG. 5 shows saRNAs candidates activating the protein expression of HMBS in liver cells. The saRNA candidates were used to transfect human hepatocellular carcinoma cells (HepG2) at a concentration of 20 nM. 72 hours later, the cells were collected for a Western blotting assay. An anti-human HMBS antibody was used to assay the protein expression of HMBS. Tubulin was used as the control to determine the accuracy of the amount of loaded protein. Mock, dsCon2, and siHMBS represent blank transfection, sequence-independent double-stranded RNA transfection, and small interference RNA control transfection, respectively.

FIG. 8 shows saRNAs candidates activating HMBS mRNA and HMBS protein in cells GM01623 of a patient suffering from acute intermittent porphyria (AIP).

FIG. 9 shows saRNA candidates activating the HMBS mRNA and HMBS protein in cells GM01624 of a patient suffering from acute intermittent porphyria (AIP).

FIG. 10 shows saRNAs candidates activating the HMBS mRNA and HMBS protein in cells GM01625 of a patient suffering from acute intermittent porphyria (AIP).

DETAILED DESCRIPTION

Figure 1:
FIG. 1. is a schematic diagram showing the promoter of HMBS gene. Region 1 and Region 2 are target sequence regions used for designing small nucleic acid molecules. TSS is the transcription start site.

In the present invention, the related terms are defined as follows.

The term "complementarity" as used herein refers to the capability of forming base pairs between two oligonucleotide strands. The base pairs are generally formed through hydrogen bonds between nucleotides in the antiparallel oligonucleotide strands. The bases of the complementary oligonucleotide strands can be paired in the Watson-Crick manner (such as A to T, A to U, and C to G) or in any other manner allowing the formation of a duplex (such as Hoogsteen or reverse Hoogsteen base pairing).

Complementarity includes complete complementarity and incomplete complementarity. "Complete complementarity" or "100% complementarity" means that each nucleotide from the first oligonucleotide strand can form a hydrogen bond with a nucleotide at a corresponding position in the second oligonucleotide strand in the double-stranded region of the double-stranded oligonucleotide molecule without "mispairing". "Incomplete complementarity" means that not all the nucleotide units of the two strands are bonded with each other by hydrogen bonds. For example, for two oligonucleotide strands each of 20 nucleotides in length in the double-stranded region, if only two base pairs in this double-stranded region can be formed through hydrogen bonds, the oligonucleotide strands have a complementarity of 10%. In the same example, if 18 base pairs in this double-stranded region can be formed through hydrogen bonds, the oligonucleotide strands have a complementarity of 90%. Substantial complementarity refers to at least about 75%, about 79%, about 80%, about 85%, about 90%, about 95%, about 99% or about 100% complementarity.

The term "oligonucleotide" or "small nucleic acid molecule" as used herein refers to polymers of nucleotides, and includes, but is not limited to, single-stranded or double-stranded molecules of DNA, RNA, or DNA/RNA hybrid, oligonucleotide strands containing regularly and irregularly alternating deoxyribosyl portions and ribosyl portions, as well as modified and naturally or nonnaturally existing frameworks for such oligonucleotides. The oligonucleotide for activating target gene transcription described herein is a small activating nucleic acid molecule.

The terms "oligonucleotide strand" and "oligonucleotide sequence" as used herein can be used interchangeably, referring to a generic term for short nucleotide sequences having less than 35 bases (including nucleotides in deoxyribonucleic acid (DNA) or ribonucleic acid (RNA)). In the present invention, an oligonucleotide strand may have any of 16 to 35 nucleotides in length.

As used herein, the term "first nucleic acid strand" may be a sense strand or an antisense strand. The sense strand of a small activating RNA refers to a nucleic acid strand contained in a small activating RNA duplex which has identity to the coding strand of the promoter DNA sequence of a target gene, and the antisense strand refers to a nucleic acid strand in the small activating RNA duplex which is complementary to the sense strand.

As used herein, the term "second nucleic acid strand" may also be a sense strand or an antisense strand. If the first oligonucleotide strand is a sense strand, the second oligonucleotide strand is an antisense strand; and if the first oligonucleotide strand is an antisense strand, the second oligonucleotide strand is a sense strand.

The term "gene" as used herein refers to all nucleotide sequences required to encode a polypeptide chain or to transcribe a functional RNA. "Gene" can be an endogenous or fully or partially recombinant gene for a host cell (for example, because an exogenous oligonucleotide and a coding sequence for encoding a promoter are introduced into a host cell, or a heterogeneous promoter adjacent to an endogenous coding sequence is introduced into a host cell). For example, the term "gene" comprises a nucleic acid sequence consisting of exons and introns. Protein-coding sequences are, for example, sequences contained within exons in an open reading frame between an initiation codon and a termination codon, and as used herein, "gene" can comprise such as a gene regulatory sequence, such as a promoter, an enhancer, and all other sequences known in the art for controlling the transcription, expression or activity of another gene, no matter whether the gene comprises a coding sequence or a non-coding sequence. In one case, for example, "gene" can be used to describe a functional nucleic acid comprising a regulatory sequence such as a promoter or an enhancer. The expression of a recombinant gene can be controlled by one or more types of heterogeneous regulatory sequences.

The term "target gene" as used herein can refer to nucleic acid sequences naturally present in organisms, transgenes, viral or bacterial sequences, can be chromosomes or extrachromosomal genes, and/or can be transiently or stably transfected or incorporated into cells and/or chromatins thereof. The target gene can be a protein-coding gene or a non-protein-coding gene (such as a microRNA gene and a long non-coding RNA gene). The target gene generally contains a promoter sequence, and the positive regulation for the target gene can be achieved by designing a small activating nucleic acid molecule having sequence identity (also called homology) to the promoter sequence, characterized as the up-regulation of expression of the target gene. "Sequence of a target gene promoter" refers to a non-coding sequence of the target gene, and the reference of the sequence of a target gene promoter in the phrase "complementary to the sequence of a target gene promoter" of the present invention refers to a coding strand of the sequence, also known as a non-template strand, i.e., a nucleic acid sequence having the same sequence as the coding sequence of the gene. "Target sequence" refers to a sequence fragment in the sequence of a target gene promoter, which is homologous or complementary to a sense oligonucleotide strand or an antisense oligonucleotide strand of a small activating nucleic acid molecule.

As used herein, the terms "sense strand" and "sense oligonucleotide strand" can be used interchangeably, and the sense oligonucleotide strand of a small activating nucleic acid molecule refers to the first nucleic acid strand having sequence homology with the coding strand of the sequence of a target gene promoter in the small activating nucleic acid molecule duplex.

As used herein, the terms "antisense strand" and "antisense oligonucleotide strand" can be used interchangeably, and the antisense oligonucleotide strand of a small activating nucleic acid molecule refers to the second nucleic acid strand which is complementary to the sense oligonucleotide strand in the small activating nucleic acid molecule duplex.

The term "coding strand" as used herein refers to a DNA strand in the target gene which cannot be used for transcription, and the nucleotide sequence of this strand is the same as that of an RNA produced from transcription (in the RNA, T in DNA is replaced by U). The coding strand of the double-stranded DNA sequence of the target gene promoter described herein refers to a promoter sequence on the same DNA strand as the DNA coding strand of the target gene.

The term "template strand" as used herein refers to the other strand complementary with the coding strand in the double-stranded DNA of the target gene, i.e., the strand that, as a template, can be transcribed into RNA, and this strand is complementary with the transcribed RNA (A to U and G to C). In the process of transcription, RNA polymerase binds to the template strand, moves along the 3'→5' direction of the template strand, and catalyzes the synthesis of the RNA along the 5'→3' direction. The template strand of the double-stranded DNA sequence of the target gene promoter described herein refers to a promoter sequence on the same DNA strand as the DNA template strand of the target gene.

The term "promoter" as used herein refers to a sequence which is spatially associated with a protein-coding or RNA-coding nucleic acid sequence and plays a regulatory role for the transcription of the protein-coding or RNA-coding nucleic acid sequence. Generally, a eukaryotic gene promoter contains 100 to 5000 base pairs, although this length range is not intended to limit the term "promoter" as used herein. Although the promoter sequence is generally located at the 5' terminus of a protein-coding or RNA-coding sequence, it may also exist in exon and intron sequences.

The term "transcription start site" as used herein refers to a nucleotide marking the transcription start on the template strand of a gene. The transcription start site may appear on the template strand of the promoter region. A gene can have more than one transcription start site.

The term "identity" or "homology" as used herein means that one oligonucleotide strand (a sense or an antisense strand) of a small activating RNA has sequence similarity to a coding strand or a template strand in a region of the promoter sequence of a target gene. As used herein, the "identity" or "homology" may be at least about 75%, about 79%, about 80%, about 85%, about 90%, about 95%, about 99% or about 100%.

The term "overhang" as used herein refers to non-base-paired nucleotides at the terminus (5' or 3') of an oligonucleotide strand, which is formed by one strand extending out of the other strand in a double-stranded oligonucleotide. A single-stranded region extending out of the 3' terminus and/or 5' terminus of a duplex is referred to as an overhang.

As used herein, the terms "gene activation", "activating gene expression", "gene up-regulation" and "up-regulating gene expression" can be used interchangeably, and mean an increase in transcription, translation, expression or activity of a certain nucleic acid as determined by measuring the transcriptional level, mRNA level, protein level, enzymatic activity, methylation state, chromatin state or configuration, translation level or the activity or state in a cell or biological system of a gene. These activities or states can be determined directly or indirectly. In addition, "gene activation", "activating gene expression", "gene up-regulation" or "up-regulating gene expression" refers to an increase in activity associated with a nucleic acid sequence, regardless of the mechanism of such activation. For example, the nucleic acid sequence plays a regulatory role as a regulatory sequence, the nucleic acid sequence is transcribed into RNA and the RNA is translated into a protein, thereby increasing the expression of the protein. Preferably, the small activating RNA molecule provided by the present invention can up-regulate gene or protein expression or increase activity by at least 10%.

As used herein, the terms "small activating RNA", "saRNA" and "small activating nucleic acid molecule" can be used interchangeably, and refer to a nucleic acid molecule that can upregulate target gene expression and can be composed of a first nucleic acid fragment (antisense strand, also referred to as antisense oligonucleotide strand) containing a nucleotide sequence having sequence homology or identity to the non-coding nucleic acid sequence (e.g., a promoter and an enhancer) of a target gene and a second nucleic acid fragment (sense strand, also referred to as sense oligonucleotide strand) containing a nucleotide sequence complementary to the first nucleic acid fragment, wherein the first nucleic acid fragment and the second nucleic acid fragment form a duplex. The small activating nucleic acid molecule can also be composed of a synthesized or vector-expressed single-stranded RNA molecule that can form a hairpin structure by two complementary regions within the molecule, wherein the first region comprises a nucleotide sequence having sequence identity to the target sequence of a promoter of a gene, and the second region comprises a nucleotide sequence which is complementary to the first region. The length of the duplex region of the small activating nucleic acid molecule is typically about 10 to about 50, about 12 to about 48, about 14 to about 46, about 16 to about 44, about 18 to about 42, about 20 to about 40, about 22 to about 38, about 24 to about 36, about 26 to about 34, and about 28 to about 32 base pairs, and typically about 10, about 15, about 20, about 25, about 30, about 35, about 40, about 45, or about 50 base pairs. In addition, the terms "saRNA", "small activating RNA", and "small activating nucleic acid molecule" also comprise nucleic acids other than the ribonucleotide, including, but not limited to, modified nucleotides or analogues.

As used herein, the term "hot spot" refers to a gene promoter region of at least 30 bp in length where functional small activating nucleic acid molecules are enriched, i.e., at least 30% of the small activating nucleic acid molecules designed to target this region is functional and can induce a 1.2-fold or more change in the mRNA expression of the target gene.

As used herein, the term "synthesis" refers to a method for synthesis of an oligonucleotide, including any method allowing RNA synthesis, such as chemical synthesis, in vitro transcription, and/or vector-based expression.

According to the present invention, the expression of HMBS gene is up-regulated by an RNA activation method, and the production of heme is promoted by increasing the expression protein of HMBS. The HMBS gene in the present invention is sometimes also called a target gene.

The method for preparing the small activating nucleic acid molecule provided by the present invention comprises sequence design and synthesis.

Small activating nucleic acid molecule can be chemically synthesized or can be obtained from a biotechnology company specialized in nucleic acid synthesis.

Generally speaking, chemical synthesis of nucleic acids comprises the following four steps: (1) synthesis of oligomeric ribonucleotides; (2) deprotection; (3) purification and isolation; and (4) desalination and annealing.

For example, the specific steps for chemically synthesizing the oligomeric nucleic acid molecules of the present invention are as follows.

(1) Synthesis of Oligomeric Nucleic Acid Molecule

Synthesis of 1 μM RNA was set in an automatic DNA/RNA synthesizer (e.g., Applied Biosystems EXPEDITE8909), and the coupling time of each cycle was also set as 10 to 15 min. With a solid phase-bonded 5'-O-p-dimethoxytriphenylmethyl-thymidine substrate as an initiator, one base was bonded to the solid phase substrate in the first cycle, and then, in the $n^{th}$ ($19 \geq n \geq 2$) cycle, one base was bonded to the base bonded in the n-$1^{th}$ cycle. This process was repeated until the synthesis of the whole nucleic acid sequence was completed.

(2) Deprotection

The solid phase substrate bonded with the oligomeric nucleic acid molecule was put into a test tube, and 1 mL of a mixed solution of ethanol and ammonium hydroxide (volume ratio: 1:3) was added to the test tube. The test tube was then sealed and placed in an incubator, and the mixture was incubated at 25-70 ° C. for 2 to 30 h. The solution containing the solid phase substrate bonded with the oligomeric nucleic acid molecule was filtered, and the filtrate was collected. The solid phase substrate was rinsed with double distilled water twice (1 mL each time), and the filtrate was collected. The collected eluent was combined and dried under vacuum for 1 to 12 h. Then the solution was added with 1 mL of a solution of tetrabutylammonium fluoride in tetrahydrofuran (1 M), let stand at room temperature for 4 to 12 h, followed by addition of 2 mL of n-butanol. Precipitate was collected to give a single-stranded crude product of saRNA by high-speed centrifugation.

(3) Purification and Isolation

The resulting crude product of saRNA was dissolved in 2 mL of aqueous ammonium acetate solution with a concentration of 1 mol/mL, and the solution was separated by a reversed-phase C18 column of high pressure liquid chromatography to give a purified single-stranded product containing the oligomeric nucleic acid molecule.

(4) Desalination and Annealing

Salts were removed by gel filtration (size exclusion chromatography). A single sense oligomeric ribonucleic acid strand and a single antisense oligomeric ribonucleic acid strand were mixed in a 1 to 2 mL of buffer (10 mM Tris, pH=7.5-8.0, 50 mM NaCl) at a molar ratio of 1:1. The solution was heated to 95° C., and was then slowly cooled to room temperature to give a solution containing the oligomeric nucleic acid molecule.

The present invention will be further illustrated with reference to specific examples and drawings below. It should be understood that these examples are merely intended to illustrate the present invention rather than limit the scope of the present invention. In the following examples, study methods without specific conditions were generally in accordance with conventional conditions, such as conditions described in Sambrook, et al., *Molecular Cloning: Laboratory Manual* (New York: Cold Spring Harbor Laboratory Press, 1989), or conditions recommended by the manufacturer.

EXAMPLES

Example 1: Design and Synthesis of Small Activating Nucleic Acid Molecule Targeting HMBS Promoter The sense sequence of HMBS gene promoter from the transcription start site (TSS) to upstream −395 bp was retrieved from the UCSC genome database with a repeat sequence (−350 to −180) being excluded from targets. With the remaining two sequences (region 1 with a length of 45 bp: −395 to −351; and region 2 with a length of 179 bp: −179 to −1) as templates, targets with a size of 19 bp were selected by moving downstream from the most upstream, a total of 27 targets were obtained in region 1 and a total of 161 targets were obtained in region 2 (FIG. 1). The target sequences were then filtered. The criteria for retaining target sequences were: (1) having a GC content between 35% and 75%; (2) with no more than 5 consecutive identical nucleotides; (3) with no more than 3 dinucleotide repeats; and (4) with no more than 3 trinucleotide repeats. After the filtration, 180 target sequences remained and their corresponding double-stranded oligonucleotide molecule were chemically synthesized based on these candidate sequences. Each of the sense strand and antisense strand in the double-stranded oligonucleotide molecule used in the study were 21 nt in length. The 19 nucleotides in the 5' region of the first ribonucleic acid strand (sense strand) of the oligonucleotide molecule had 100% sequence identity to the target sequence of the promoter, and the 3' terminus of the first ribonucleic acid strand contained a TT sequence. The 19 nucleotides in the 5' region of the second ribonucleic acid strand were complementary to the first ribonucleic acid strand sequence, and the 3' terminus of the second ribonucleic acid strand contained a TT sequence. The aforementioned two strands of the oligonucleotide molecule were mixed at a molar ratio of 1:1, and after annealing, a double-stranded oligonucleotide molecule was formed.

Example 2: Screening of saRNAs Targeting HMBS Promoter

(1) Cell Culture and Transfection

Human hepatocarcinoma cell lines Huh7 and HepG2 were cultured in DMEM media (Gibco). Human embryonic liver cells CCC-HEL-1 and human hepatocarcinoma cells Li-7 were cultured in RPMI-1640 media (Gibco), which all contained 10% of calf serum (Sigma-Aldrich) and 1% of penicillin/streptomycin (Gibco). The cells were cultured at 5% $CO_2$ and 37° C. According to the instructions of the manufacturer, RNAiMax (Invitrogen, Carlsbad, CA) was used to transfect double-stranded oligomeric nucleic acid molecule at a concentration of 10 nM (unless otherwise specified) by reverse transfection.

(2) One-step RT-qPCR

At the end of transfection, the media were discarded, and each well was washed with 150 μL of PBS once. After discarding PBS, 50 μL of cell lysis buffer was added into each well, and incubated at room temperature for 5 minutes. 1 μof the resulted cell lysis was taken from each well and subjected to qPCR analysis on a LightCycler® 480 system (Roche) by using a one-step TB Green™ PrimeScrip™ RT-PCR kit II (Takara,RR086A).Each transfection sample was amplified in 3 repeat wells. PCR reaction conditions are shown in Table 1.

TABLE 1

PCR reaction preparation

| Reagent | Volume/Reaction |
| --- | --- |
| 2 × One-step TB Green RT-PCR buffer 4 | 2.5 μL |
| PrimeScript 1 step enzyme mixture 2 | 0.2 μL |
| Mixture of forward and reverse primers (5 μM) | 0.4 μL |
| No RNase dH₂O | 1.4 μL |
| Crude lysate (RNA) | 0.5 μL |
| Sum | 5 μL |

Reaction conditions were as follows: reverse transcription reaction (stage 1): 5 min at 42° C., 10 s at 95° C.; PCR reaction (stage 2): 5 s at 95° C., 20 s at 60° C., 45 cycles of amplification. HPRT1 and TBP were used as internal reference genes. PCR primers used for amplifying HMBS, HPRT1 and TBP genes are shown in Table 2, wherein HMBS was amplified using the HMBS F1/R1 primer pair.

TABLE 2

Primer sequences for RT-qPCR analysis

| Primer | Sequence No. | Sequence (5'-3') |
| --- | --- | --- |
| HMBS F1 | SEQ ID NO: 5 | ACAGCTATGAAGGATGGGCAA |
| HMBS R1 | SEQ ID NO: 6 | ATCTTCATGCTGGGCAGGGA |
| HPRT1 F | SEQ ID NO: 7 | ATGGACAGGACTGAACGTCTT |
| HPRT1 R | SEQ ID NO: 8 | TCCAGCAGGTCAGCAAAGAA |
| TBP F | SEQ ID NO: 9 | ATAATCCCAAGCGGTTTGCT |
| TBP R | SEQ ID NO: 10 | CTGCCAGTCTGGACTGTTCT |

In order to calculate the expression value ($E_{rel}$) of HMBS (target gene) of a saRNA-transfected sample relative to control treatment (Mock), the Ct values of the target gene and the two internal reference genes were substituted into formula 1 for calculation.

$$E_{rel}=2^{(CtT_m-CtTs)}/((2^{(CtR1_m-CtR1s)}*2^{(ctR2_m-CtR2_s)})^{(1/2)})\quad\text{(formula 1)}$$

wherein $CtT_m$ was the Ct value of the target gene from the Mock sample; CtTs was the Ct value of the target gene from the saRNA-treated sample; $CtR1_m$ was the Ct value of the internal reference gene 1 from the Mock-treated sample; CtR1s was the Ct value of the internal reference gene 1 from the saRNA-treated sample; $CtR2_m$ was the Ct value of the internal reference gene 2 from the Mock-treated sample; and $CtR2_s$ was the Ct value of the internal reference gene 2 from the saRNA-treated sample.

(3) Screening of Functional saRNAs

In order to obtain saRNAs capable of activating HMBS transcription, 180 double-stranded oligonucleotide molecules were transfected into Huh7 cells at a concentration of 10 nM. 72 hours later, and according to the same method as described above, cells were lysed and subjected to one-step RT-qPCR analysis to obtain the relative expression value of HMBS gene for each saRNA-treated sample when compared with Mock treatment. The results indicated that 19 saRNAs exhibited activating activity. These double-stranded oligomeric nucleic acid molecules with activating activity are referred to as functional saRNAs.

Figure 2:
FIG. 2. shows changes in expression level of HMBS mRNA mediated by small nucleic acid molecules. One hundred and eighty promoter-targeting saRNAs were individually transfected into human hepatocellular carcinoma cells (Huh7) at a concentration of 10 nM. 72 hours later, the expression level of HMBS mRNA was analyzed by a one-step RT-PCR assay. The drawing shows the relative fold changes of the expression level of HMBS caused by each of the 180 saRNA sorted by fold change in descending order.
Figure 3:
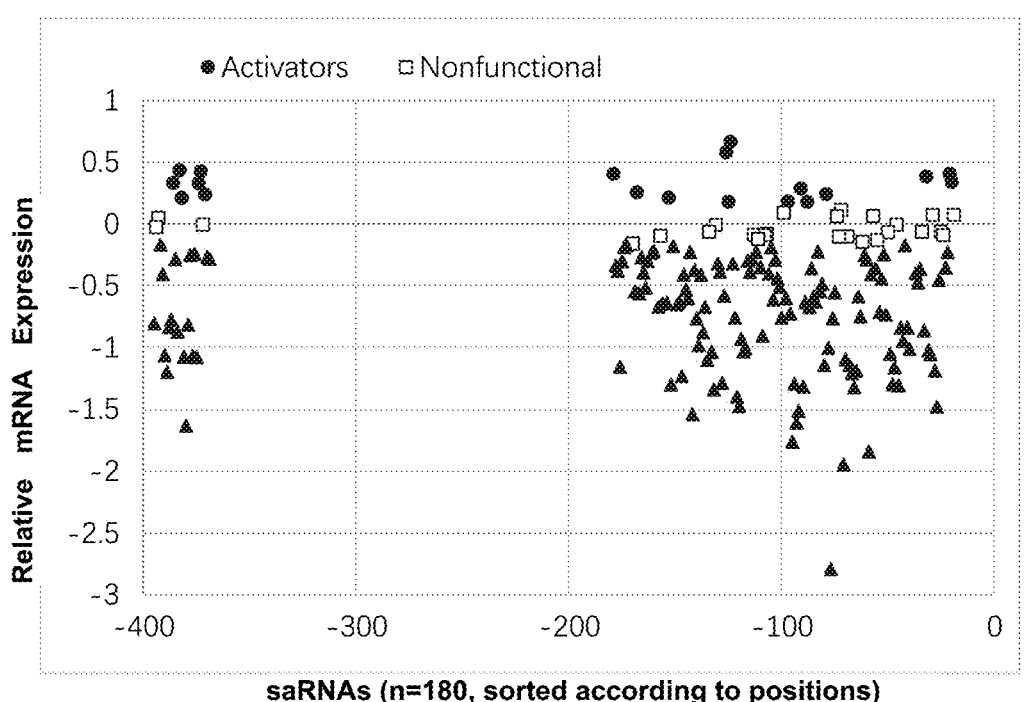
FIG. 3 shows changes in the HMBS mRNA expression mediated by small nucleic acid molecules. Cells Huh7 were transfected by 180 promoter-targeting small nucleic acid molecules (saRNAs) were individually transfected in Huh7 cells at a concentration of 10 nM, 72 hours later, the expression level of HMBS mRNA was analyzed by a one-step RT-PCR assay. The drawing shows fold changes in expression level of HMBS mRNA caused by each saRNA relative to control (Mock) treatment. The small nucleic acid molecules are sorted by their target location on the promoter of HMBS gene from most upstream to the TSS.

FIG. 2 and FIG. 3 further show the activity distribution of the saRNAs for HMBS and the changes in the mRNA expression of HMBS mediated by the saRNAs.

TABLE 4

Active saRNA Sequences, Active Target Sequences Thereof and Changes in mRNA Expression of HMBS

| saRNA | Functional target sequence (5'-3') | Sense sequence (5'-3') | Antisense sequence (5'-3') | Fold of change in mRNA expression of HMBS |
| --- | --- | --- | --- | --- |
| RAG5-124 | CCATAGAAGCTGCACTACT (SEQ ID No: 11) | CCAUAGAAGCUGCACUACUTT (SEQ ID No. 30) | AGUAGUGCAGCUUCUAUGGTT (SEQ ID No. 49) | 1.59 |
| RAG5-126 | CGCCATAGAAGCTGCACTA (SEQ ID No: 12) | CGCCAUAGAAGCUGCACUAUT (SEQ ID No. 31) | UAGUGCAGCUUCUAUGGCGTT (SEQ ID No. 50) | 1.49 |
| RAG5-383 | CATAGTGAGGCCACCTCCC (SEQ ID No: 13) | CAUAGUGAGGCCACCUCCCTT (SEQ ID No. 32) | GGGAGGUGGCCUCACUAUGTT (SEQ ID No. 51) | 1.35 |
| RAG5-373 | CCACCTCCCCGCTGTCTCT (SEQ ID No: 14) | CCACCUCCCCGCUGUCUCUTT (SEQ ID No: 33) | AGAGACAGCGGGGAGGUGGTT (SEQ ID No: 52) | 1.34 |

TABLE 4-continued

Active saRNA Sequences, Active Target Sequences Thereof and Changes in mRNA
Expression of HMBS

| saRNA | Functional target sequence (5'-3') | Sense sequence (5'-3') | Antisense sequence (5'-3') | Fold of change in mRNA expression of HMBS |
|---|---|---|---|---|
| RAG5-179 | TGCTGCCTATTTCAAGGTT (SEQ ID No: 15) | UGCUGCCUAUUUCAAGGUUTT (SEQ ID No: 34) | AACCUUGAAAUAGGCAGCATT (SEQ ID No: 53) | 1.33 |
| RAG5-21 | CCTCCCCTTCGAGGGAGGG (SEQ ID No: 16) | CCUCCCCUUCGAGGGAGGGTT (SEQ ID No: 35) | CCCUCCCUCGAAGGGGAGGTT (SEQ ID No: 54) | 1.33 |
| RAG5-32 | AGAGGGAGGGACCTCCCCT (SEQ ID No: 17) | AGAGGGAGGGACCUCCCCUTT (SEQ ID No: 36) | AGGGGAGGUCCCUCCCUCUTT (SEQ ID No: 55) | 1.30 |
| RAG5-20 | CTCCCCTTCGAGGGAGGGC (SEQ ID No: 18) | CUCCCCUUCGAGGGAGGGCTT (SEQ ID No: 37) | GCCCUCCCUCGAAGGGGAGTT (SEQ ID No: 56) | 1.26 |
| RAG5-386 | CAACATAGTGAGGCCACCT (SEQ ID No: 19) | CAACAUAGUGAGGCCACCUTT (SEQ ID No: 38) | AGGUGGCCUCACUAUGUUGTT (SEQ ID No: 57) | 1.26 |
| RAG5-374 | GCCACCTCCCCGCTGTCTC (SEQ ID No: 20) | GCCACCUCCCCGCUGUCUCTT (SEQ ID No: 39) | GAGACAGCGGGGAGGUGGCTT (SEQ ID No: 58) | 1.26 |
| RAG5-91 | CTGGGGAATGGGGTGGTCG (SEQ ID No: 21) | CUGGGGAAUGGGGUGGUCGTT (SEQ ID No: 40) | CGACCACCCCAUUCCCCAGTT (SEQ ID No: 59) | 1.22 |
| RAG5-168 | TCAAGGTTGTAGCAAAGCT (SEQ ID No: 22) | UCAAGGUUGUAGCAAAGCUTT (SEQ ID No: 41) | AGCUUUGCUACAACCUUGATT (SEQ ID No: 60) | 1.19 |
| RAG5-79 | GTGGTCGAATGGGGAGGTC (SEQ ID No: 23) | GUGGUCGAAUGGGGAGGUCTT (SEQ ID No: 42) | GACCUCCCCAUUCGACCACTT (SEQ ID No: 61) | 1.18 |
| RAG5-371 | ACCTCCCCGCTGTCTCTAT (SEQ ID No: 24) | ACCUCCCCGCUGUCUCUAUTT (SEQ ID No: 43) | AUAGAGACAGCGGGGAGGUTT (SEQ ID No: 62) | 1.18 |
| RAG5-153 | AGCTAAGTTTGAACAGAGC (SEQ ID No: 25) | AGCUAAGUUUGAACAGAGCTT (SEQ ID No: 44) | GCUCUGUUCAAACUUAGCUTT (SEQ ID No: 63) | 1.16 |
| RAG5-382 | ATAGTGAGGCCACCTCCCC (SEQ ID No: 26) | AUAGUGAGGCCACCUCCCCTT (SEQ ID No: 45) | GGGGAGGUGGCCUCACUAUTT (SEQ ID No: 64) | 1.16 |
| RAG5-97 | TCACAGCTGGGGAATGGGG (SEQ ID No: 27) | UCACAGCUGGGGAAUGGGGTT (SEQ ID No: 46) | CCCCAUUCCCCAGCUGUGATT (SEQ ID No: 65) | 1.13 |
| RAG5-88 | GGGAATGGGGTGGTCGAAT (SEQ ID No: 28) | GGGAAUGGGGUGGUCGAAUTT (SEQ ID No: 47) | AUUCGACCACCCCAUUCCCTT (SEQ ID No: 66) | 1.13 |
| RAG5-125 | GCCATAGAAGCTGCACTAC (SEQ ID No: 29) | GCCAUAGAAGCUGCACUACTT (SEQ ID No: 48) | GUAGUGCAGCUUCUAUGGCTT (SEQ ID No: 67) | 1.13 |

Example 3: saRNAs Induced Expression of HMBS Gene in Different Cell Lines

Figure 4A:
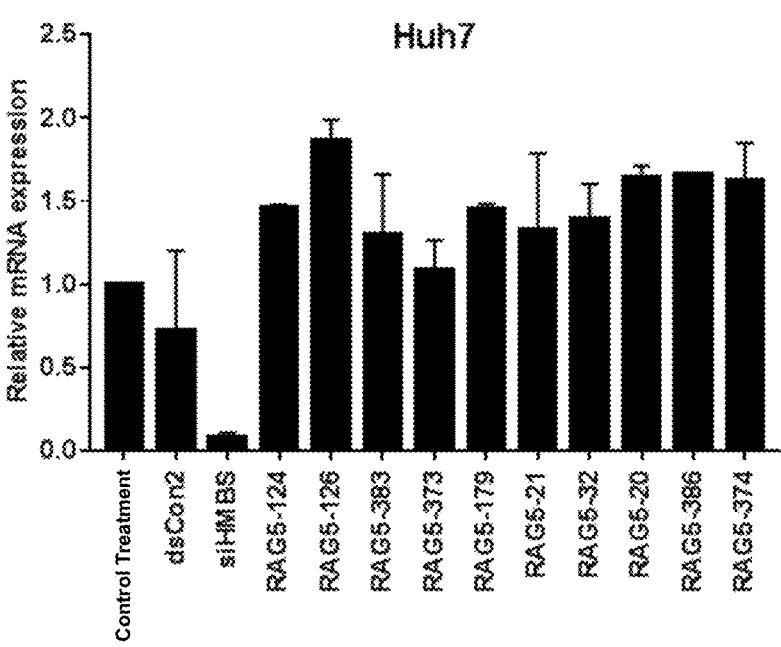
FIG. 4A, human hepatocellular carcinoma cells (HepG2)
Figure 4B:
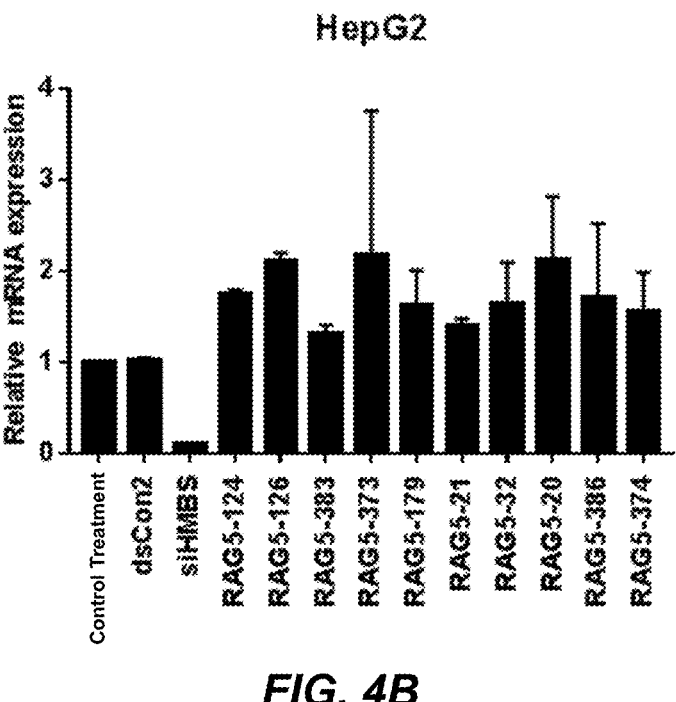
FIG. 4B, and human embryonic liver cells (CCC-HEL-1)
Figure 4C:
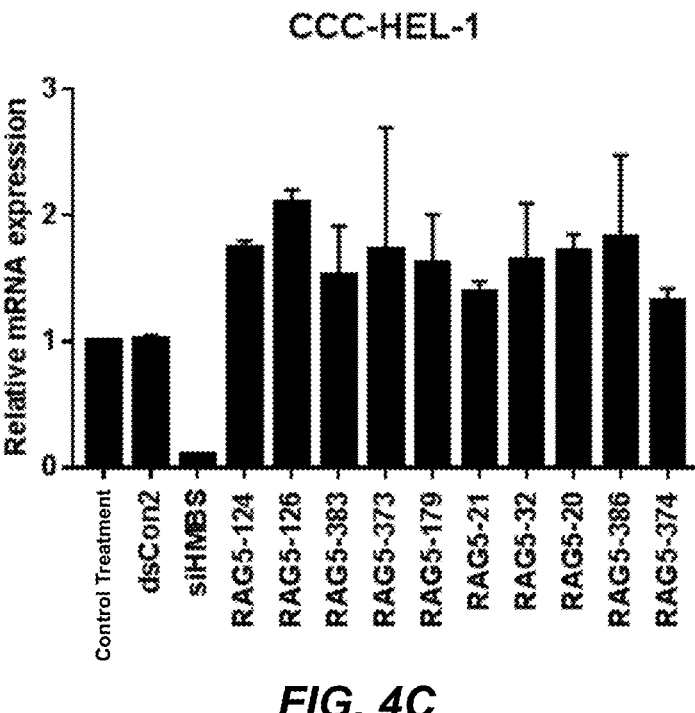
FIG. 4C. After 72 hours, cells were collected and the RNA was extracted using a Qiagen RNeasy kit. After reverse transcription, a 7500FAST real-time PCR system was used to perform qPCR amplification on HMBS gene. Co-currently, HPRT1 and TBP genes were amplified and used as internal references. Mock, dsCon2 (sense strand: 5'-ACUACUGAGUGACAGUAGATT-3' (SEQ ID NO : 68), antisense strand: 5'-UCUACUGUCA-CUCAGUAGUTT-3' (SEQ ID NO: 69)) and siHMBS (sense strand: 5'-CCUGUUUACCAAGGAGCUUTT-3' (SEQ ID No: 3), antisense strand: 5'-AAGCUCCUUG-GUAAACAGGTT-3' (SEQ ID No: 4)) were used respectively for blank transfection, sequence-independent double-stranded RNA transfection, and small interference RNA (siRNA) control transfection.

The saRNAs (n=13, final concentrations: 20 nM) shown in Table 4 were transfected into human hepatocellular carcinoma cells Huh[7] and HepG2, and human embryonic liver cells CCC-HEL-1 according to the method described in Example 2. 72 hours after the transfection, the cells were collected, and RNAs were extracted using a Qiagen RNeasy kit. After reverse transcription, a 7500FAST real-time PCR system was used to perform qPCR amplification on the HMBS gene. At the same time, HPRT1 and TBP genes were amplified as internal references. Mock, dsCon2 and siHMBS represent blank and a control dsRNA transfection, and a small interference RNA control transfection, respectively. The PCR result was analyzed according to the method described in Example 2. As shown in FIG. 4, all the candidate saRNAs can promote HMBS mRNA expression levels in different cell lines.

Example 4: saRNAs Induced Protein Expression of HMBS

Figures 5A, 5B:
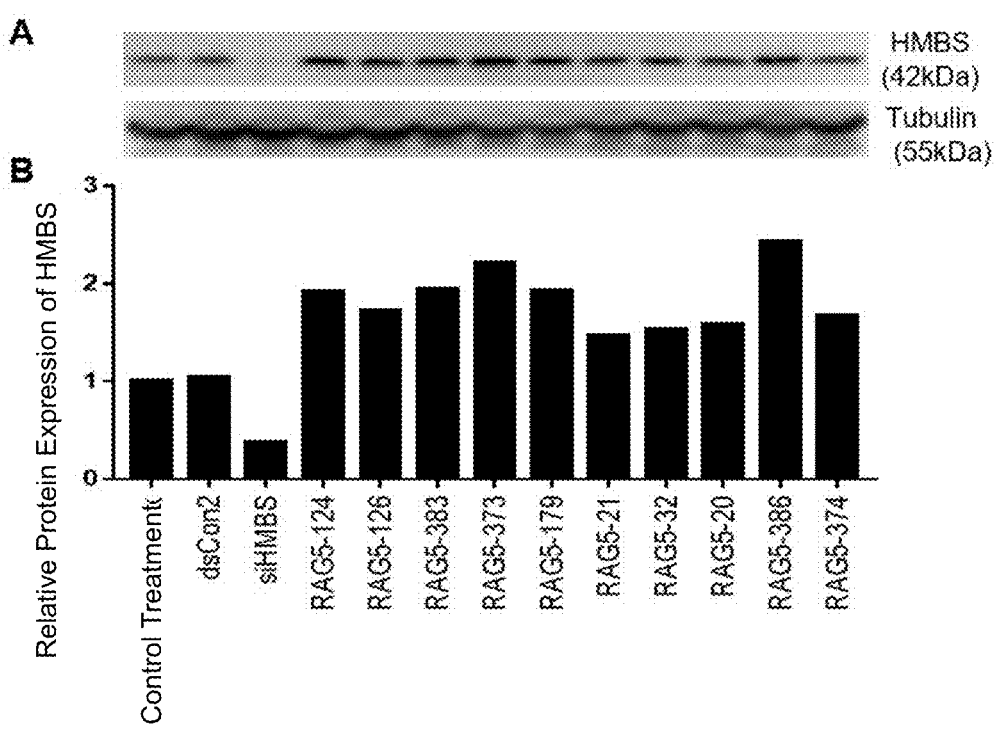
FIG. 5A shows scanned images of Western blotting membranes.
FIG. 5B shows the relative value of the HMBS band intensity of each treatment compared with that of Mock treatment obtained by using ImageJ software to quantitatively analyze the bands in FIG. 5A.

The saRNAs (final concentration: 20 nM) shown in FIG. 5 were used to reversely transfect human hepatocellular carcinoma cells HepG2. 72 hours later, the cells were collected and lysed with an appropriate amount of cell lysis buffer (1×RIPA buffer, Cell Signaling Technology) containing protease inhibitor. Protein quantification was performed by using the BCA method, polyacrylamide gel electrophoresis separation was then performed, and the protein was transferred to a 0.45 μm PVDF membrane. Rabbit monoclonal anti-HMBS (ABCAM, AB 129092) α/β-tubulin antibody (Cell Signaling Technology, 2148s) was used as a primary antibody to detect blots. Anti-rabbit IgG, HRP-linked antibody (Cell Signaling Technology) was used as a secondary antibody. Image Lab (BIO-RAD, Chemistry Doc™ MP Imaging System) was used for scanning to detect signals. As shown in FIG. 5, the saRNAs candidates increased the protein expression of HMBS in the cells HepG2 by nearly two-fold, and some induced protein expression by 2.5 fold. The effect of the activating saRNAs in activating the protein expression of HMBS in liver cells is significant.

Example 5: saRNAs Enhanced HMBS Enzymatic Activity

AIP is a disease caused by the in vivo accumulation of δ-aminolevulinic acid (ALA) and PBG (porphobilinogen), and insufficient heme synthesis as a result of the defect or insufficient activity of the third enzyme (hydroxymethylbilane synthase (HMBS)) in the heme synthesis pathway. ALA is a simple endogenous five-carbon chemical substance, and it participates in the biosynthesis of heme in vivo. As a precursor of heme, ALA produces proto-porphyrin IX (abbreviated as PPIX) with a strong photosensitive effect in mitochondria under the action of a series of enzymes such as ALA dehydratase. As an intermediate for the last step of heme biosynthesis, PPIX is bonded with Fe ions to produce heme. Normally, the heme biosynthesis pathway is regulated by a negative feedback mechanism, that is the synthesis of ALA is regulated by the amount of heme in cells, so there is no excessive ALA accumulated in the body. When exogenous ALA is added into cells, the heme synthesis pathway in the cells can convert ALA into PPIX. The content of PPIX can be detected by a fluorescence method. Therefore, the activity of HMBS and the amount of biosynthesized heme can be indirectly reflected by detecting the fluorescence intensity of PPIX (Sassa, et al., *J Exp Med* 1975; 142:722-731, Divaris, et al., *Am J Pathol* 1990; 136:891-897, Kennedy, et al., *J Photochem Photobiol.* 1992; 14:275-292). This detection method is called ALA conversion analysis.

Human embryonic liver cells CCC-HEL-1 were inoculated into 6-well plates at a concentration of $2 \times 10^5$ cells/well. RNAiMax (Invitrogen, Carlsbad, CA) and the saRNAs shown in FIG. 6 were used to transfect cells at a final concentration of 20 nM according to the reverse transfection method provided by the instructions of the manufacturer. 48 hours after the transfection, the cells were treated with 1 mM of ALA for 0 h (baseline) and at 24 h. On the third day after the transfection, the cells were collected into 1.5 ml centrifuge tubes. A fraction of each sample was taken out to lyse the cells with 300 μl of 1 N 1:1 MeOH-PCA on ice for 10 minutes. After 10 minutes of centrifuging at 10,000 g and 4° C., 100 μl of supernatant was taken out and added into black bottom 96-well plates. A multifunctional microplate reader (TECAN Infintie M200PRO) was used to detect fluorecence intensity with 400 nM exciting light and 660 nM emitted light. The cells in the other part of each sample were lysed with 1×RIPA lysis buffer (Cell Signaling Technology), and the BCA method was then employed to assess protein concentration. Finally, the data were normalized with the ratio of fluorescence intensity/protein concentration.

Figure 6:
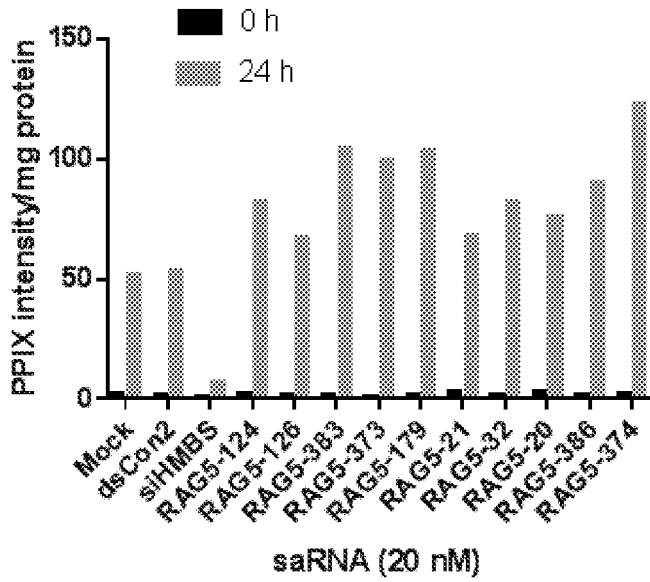
FIG. 6 shows PPIX fluorescence intensities per unit (mg) of protein obtained by ALA conversion analysis. The saR-NAs shown were used to transfect human embryonic liver cells (CCC-HEL-1). 48 hours later, an ALA substrate was added into the cells. Before the addition of the substrate (0 h) and 24 hours after addition of the substrate (24 h), the cells were collected for analyzing PPIX fluorescence intensities. Co-currently, the cells were lysed to determine protein concentrations. Mock, dsCon2, and siHMBS represent blank transfection, sequence-independent double-stranded RNA transfection, and small interference RNA control transfection, respectively. The axis Y is PPIX fluorescence intensities per unit (mg) of protein.

As shown in FIG. 6, compared to the control groups Mock and dsCon2, the fluorescence intensity per unit protein concentration in saRNA transfected cells increased significantly, indicating that HMBS gene activation caused by the saRNAs increased HMBS enzymatic activity and promoted the synthesis of heme.

Example 6: saRNAs Dose-Dependently Induced mRNA and Protein Expressions of HMBS Gene and Increased HMBS Enzynmatic Activity Cells were cultured as described in Example 2. Human hepatocarcinoma cells (Li-7) were inoculated into 6-well plates at $2 \times 10^5$ cells/well. saRNAs (RAG5-386) as shown in FIG. 7 were transfected into the cells at final concentrations of 1 nM, 10 nM, 20 nM, 50 nM, and 100 nM, using RNAiMax (Invitrogen, Carlsbad, CA) according to the reverse transfection method provided by the instructions of the manufacturer in triplicates for different assays. One group of cells were transfected for 24 h, the transfected cells were treated with 1 mM of ALA for 48 h, then the cells were collected to analyze the fluorescence intensity of PPIX. At the same time, the cells were lysed to determine protein concentration. Two other groups of cells were transfected for 72 h, these cells were collected for assessing HMBS mRNA and HMBS protein expression. The mRNA extraction and protein lysis quantification method are as described in Example 3 and Example 4.

Figure 7A:
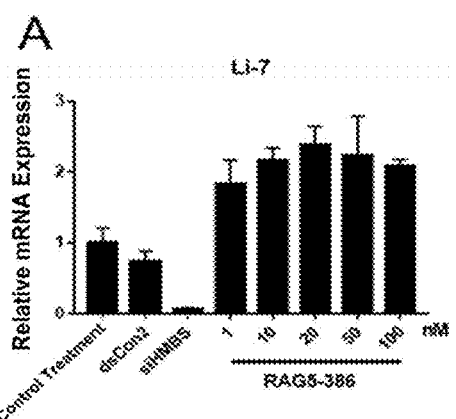
FIG. 7A shows saRNA concentrations used to transfect human hepatocarcinoma cells Li-7; 72 hours later, cells were collected, and RNA was extracted using a Qiagen RNeasy kit; after reverse transcription, a 7500FAST real-time PCR system was used to perform qPCR amplification on the HMBS gene; co-currently, HPRT1 gene was amplified as an internal reference. The upper drawing of FIG. 7B shows the saRNAs used to transfect human hepatocarcinoma cells (Li-7) at the indicated concentrations; 72 hours later, the cells were collected for a Western blotting assay; an anti-human HMBS antibody was used to assay the protein expression of HMBS; tubulin was used as a control to determine the accuracy of loaded protein amount. The bottom drawing of FIG. 7B shows a relative value of the HMBS band intensity of each treatment compared to Mock treatment obtained by using ImageJ software to quantita-tively analyze the bands in the FIG. 7A. M: Mock treatment; C: dsCon2 treatment.
Figure 7B:
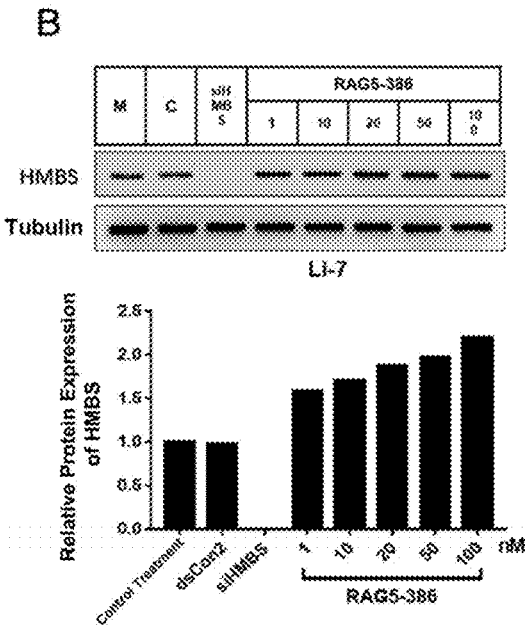
FIG. 7 shows saRNA candidates activating the HMBS mRNA and HMBS protein expression in Li-7 cells and PPIX fluorescence intensities per unit (mg) of protein obtained by ALA conversion analysis.
FIG. 7C shows the saRNAs used to transfect human hepatocarcinoma cells (Li-7) at the indi-cated concentrations; 24 hours later, ALA substrate was added to cells at 24 hours and at 48 hours cells were collected for analyzing PPIX fluorescence intensities; and co-currently cells were lysed to determine protein concen-trations. Mock, dsCon2 and siHMBS represent blank trans-fection, sequence-independent double-stranded RNA trans-fection, and small interference RNA control transfection, respectively.
Figure 7C:
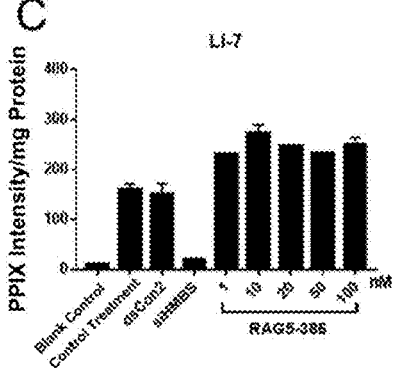

As shown in FIG. 7, with increasing saRNA (RAG5-386) dosage, HMBS mRNA and HMBS protein expression was increased. FIG. 7A shows mRNA expression after saRNA (RAG5-386) treatment. Comparing to control treatment, the mRNA expression in the siHMBS group decreased by more than 90%, indicating the effectiveness of the transfection system in the study. The saRNA (RAG5-386) group could activate HMBs by two-fold with the activating effect peaked at a saRNA (RAG5-386) treatment concentration of 20 nM. FIG. 7B shows protein expression after saRNA (RAG5-386) treatment. Compared with control treatments, HMBS protein expression was gradually upregulated with increasing concentrations of saRNA (RAG5-386), with all concentrations having an at least 1.5-fold induction and showing a dose-dependence. FIG. 7C shows changes in PPIX fluorescence intensity after treatment by the saRNA (RAG5-386). PPIX fluorescence intensity was increased with all concentrations of saRNA (RAG5-386). These results indicate that the saRNA (RAG5-386) promotes HMBS gene activation, increases HMBS enzymatic activity, and promotes the synthesis of heme.

Example 7: saRNAs Induced mRNA and Protein Expressions of HMBS Gene AIP Patients' Cells GM01623

GM01623, GM01624 and GM01625 cells (purchased from Coriell Institute, Camden, NJ, USA) were cultured in MEM media (Gibco), all of which contained 15% of calf serum (Sigma-Aldrich), 1% of NEAA (non-essential amino acids, purchased from Thermo Fisher; Item No. 11140050), and 1% of penicillin/streptomycin (Gibco). The cells were cultured at 5% $CO_2$ and 37° C. The cells GM01623 were inoculated into 6-well plates at $1 \times 10^5$ cells/well and transfected using RNAiMax at a final transfection concentration of 20 nM. 72 hours after the transfection, the cells were collected. The cell mRNA extraction and protein lysis quantification method are as described in Example 3 and Example 4.

Figure 8A:
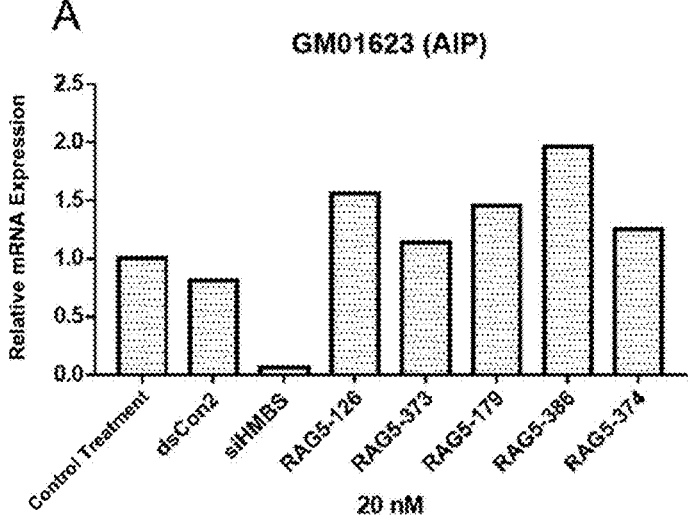
FIG. 8A shows saRNAs used to transfect cells GM01623 at a final concentration of 20 nM; 72 hours later, the cells were collected, and the RNAs were extracted using a Qiagen RNeasy kit; after reverse transcription, a 7500FAST real-time PCR system was used to perform qPCR amplification on HMBS gene; co-currently, HPRT1 and TBP genes were amplified as internal references.
Figure 8B:
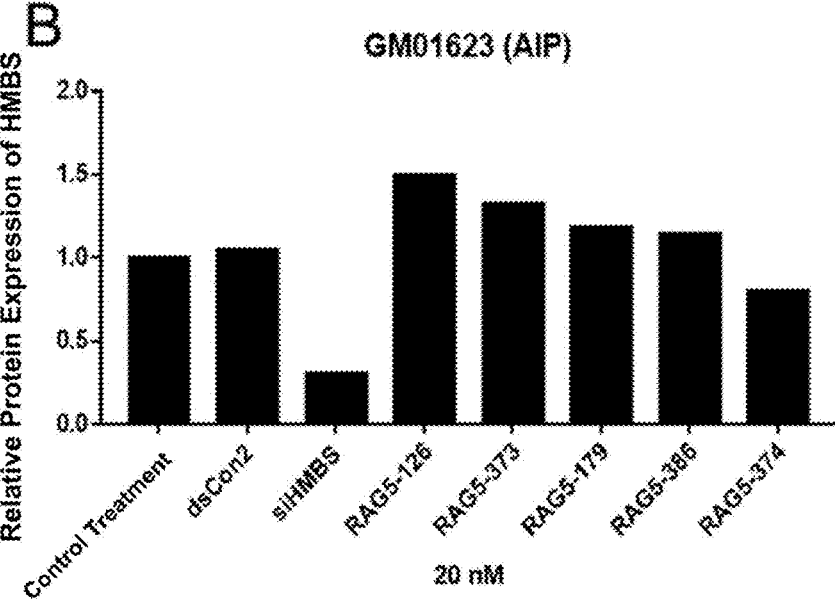
FIG. 8B shows the saRNAs used to transfect cells GM01623 at a final concentration of 20 nM; 72 hours later, the cells were collected for a Western blotting assay; an anti-human HMBS antibody was used to assay the protein expression of HMBS; and at the same time, tubulin was used as the control to determine the accuracy of loaded protein. Mock, dsCon2, and siHMBS represent blank transfection, control dsRNA transfection, and small interference RNA control transfection, respectively.

As shown in FIG. 8, the saRNA candidates induced HMBS mRNA and HMBS protein expression in the cells GM01623 of an AIP patient. FIG. 8A shows the mRNA expression after treatment by the saRNA candidates. Compared to control treatment, the mRNA expression in the siHMBS group decreased by more than 90%, indicating the effectiveness of the transfection system in the study. The relative mRNA expression in all cells treated by saRNAs was higher than the control treatment group, and the expression values in the five groups, RAG5-126, RAG5-373, RAG5-179, RAG5-386 and RAG5-374 were increased by 56%, 14%, 45%, 96% and 25%, respectively, indicating that all the saRNA candidates in the present invention can activate HMBS mRNA expression. FIG. 8B shows protein expression after saRNA candidate treatment. Compared with control, the protein expression after treatment in the groups RAG5-126, RAG5-373, RAG5-179 and RAG5-386 was increased to different extent, of which, RAG5-126 increased HMBS protein by 50%. Therefore, all of the saRNA candidates disclosed by the present invention can activate the protein expression of HMBS.

Example 8: saRNAs Induced mRNA and Protein Expressions of HMBS Gene in AIP Patients' Cells GM01624

Figure 9A:
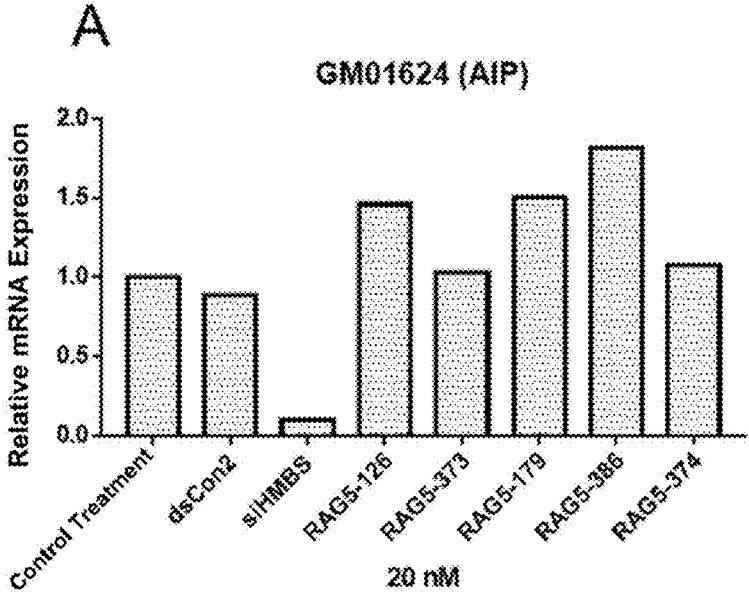
FIG. 9A shows the saRNAs used to transfect cells GM01624 at a final concentration of 20 nM; 72 hours later, the cells were collected, and the RNAs were extracted using a Qiagen RNeasy kit; after reverse transcription, a 7500FAST real-time PCR system was used to perform qPCR amplification on HMBS gene; and at the same time, HPRT1 and TBP genes were amplified as internal references.
Figure 9B:
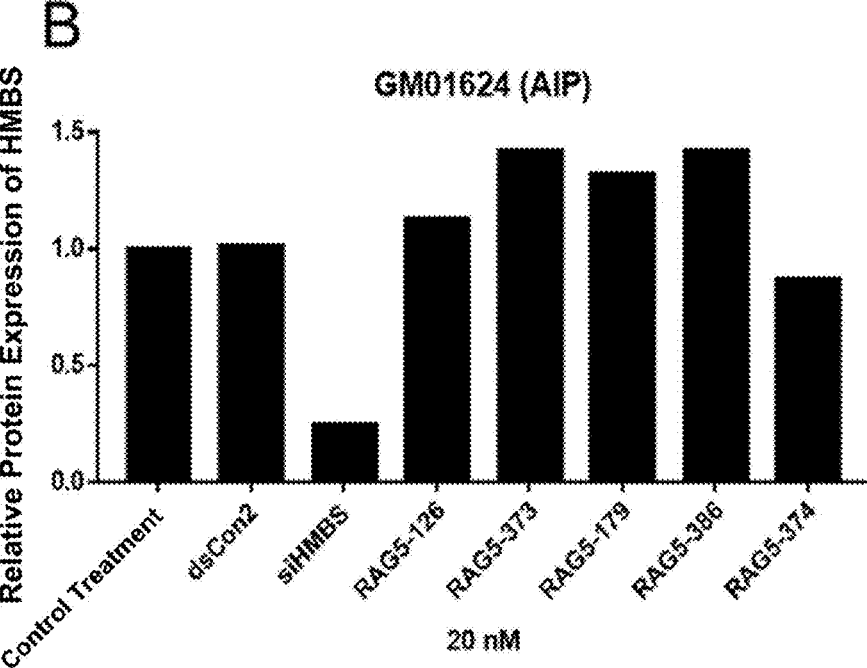
FIG. 9B shows the saRNAs used to transfect cells GM01624 at a final concentration of 20 nM; 72 hours later, the cells were collected for a Western blotting assay; an anti-human HMBS antibody was used to assay the protein expression of HMBS; and at the same time, tubulin was used as a control for protein loading. Mock, dsCon2, and siHMBS represent blank transfection, control dsRNA transfection, and small interference RNA control transfection, respectively.

The conditions for culturing and transfecting cells GM01624 are as described in Example 7, and cell mRNA extraction and protein lysis quantification method are as described in Example 3 and Example 4. As shown in FIG. 9, saRNA candidates could induce HMBS mRNA and HMBS protein expression in the cells GM01624 of an AIP patient. FIG. 9A shows the mRNA expression after treatment by the saRNA candidates. Compared with control treatment, the mRNA expression in the siHMBS group was decreased by 90%, indicating the effectiveness of the transfection system in the study. The relative mRNA expression after treatment by the saRNAs was higher than the control treatment group, and the expression values in the three groups RAG5-126, RAG5-179 and RAG5-386 are increased by more than 50%, indicating that the saRNA candidates disclosed by the present invention can activate HMBS mRNA expression. FIG. 9B shows the protein expression after treatment with saRNA candidates. Compared to control treatment, the protein expression in the groups RAG5-126, RAG5-373, RAG5-179 and RAG5-386 after saRNAs treatment was increased indicating that the saRNA candidates disclosed by the present invention can activate the HMBS protein expression.

Example 9: saRNAs Induced mRNA and Protein Expressions of HMBS Gene in AIP Patient Cells GM01625

Figure 10A:
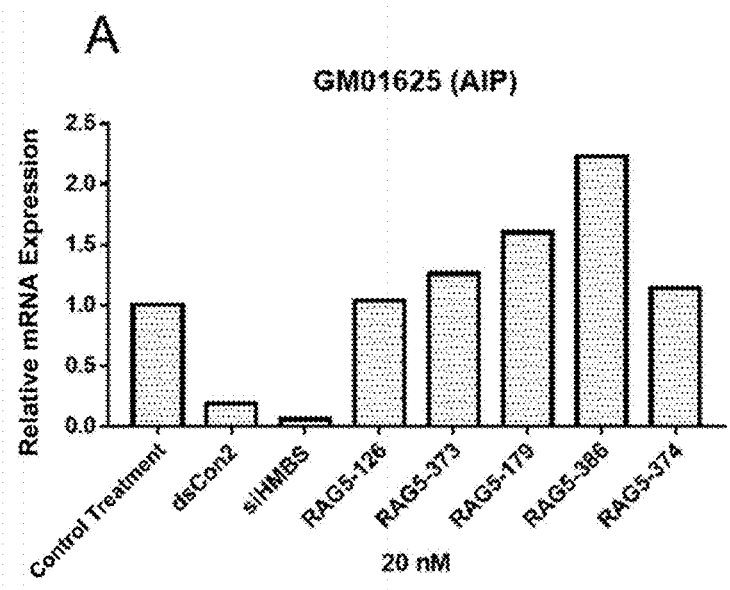
FIG. 10A shows saRNAs used to transfect cells GM01625 at a final concentration of 20 nM; 72 hours later, the cells were collected, and the RNAs were extracted using a Qiagen RNeasy kit; after reverse transcription, a 7500FAST real-time PCR system was used to perform qPCR amplification on HMBS gene; and at the same time, HPRT1 and TBP genes were amplified as internal references.
Figure 10B:
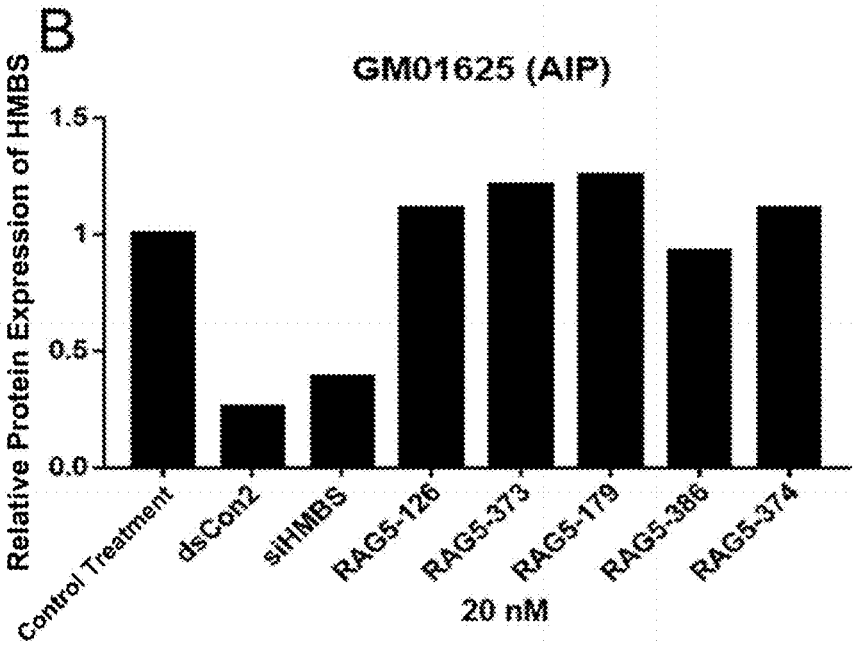
FIG. 10B shows saRNAs used to transfect cells GM01625 at a final concentration of 20 nM; 72 hours later, the cells were collected for a Western blotting assay; an anti-human HMBS antibody was used to assay the protein expression of HMBS; and at the same time, tubulin was used as a control for protein loading. Mock, dsCon2 and siHMBS are blank transfection, control dsRNA transfection, and small interference RNA control transfection, respectively.

The conditions for culturing and transfecting cells GM01625 are as described in Example 7 and cell mRNA extraction and protein lysis quantification method are as described in Example 3 and Example 4. As shown in FIG. 10, the candidate saRNAs could promote HMBS mRNA and HMBS protein expression in the cells GM01625 of an AIP patient. FIG. 10A shows the HMBS mRNA expression after treatment by saRNAs candidates. Compared to control treatment, the mRNA expression in the siHMBS group is decreased by more than 90%, indicating the effectiveness of the transfection system in the study. The relative mRNA expression after treatment by all the saRNAs was higher compared to the control treatment group, and the expression values in the groups RAG5-126, RAG5-373, RAG5-179, RAG5-386 and RAG5-374 were increased by 4%, 26%, 60%, 123% and 14%, respectively, with RAG5-386 being extremely potent, indicating that the saRNA candidates provided by the present invention can activate HMBS mRNA expression and have an activating effect. FIG. 10B shows the protein expression after treatment with saRNA candidates. Compared to control treatment, the protein expression was all increased after treatment by RAG5-126, RAG5-373, RAG5-179 and RAG5-374, indicating that the saRNA candidates provided by the present invention can activate the protein of HMBS.

Altogether, a plurality of saRNAs capable of activating the expression of HMBS gene were identified through high-throughput screening of saRNAs targeting the HMBS gene promoter. These saRNAs promote heme production by upregulating the expression of HMBS mRNA and HMBS protein. These results suggest that the saRNAs targeting the HMBS gene promoter can be a therapeutic strategy for AIP treatment.

---

What is claimed is:

1. A small activating RNA (saRNA) comprising: a first nucleic acid strand and a second nucleic acid strand, wherein the first nucleic acid strand has at least 90% homology or complementarity to a nucleotide sequence selected from SEQ ID NOs:11-20 in the promoter of HMBS gene, the second nucleic acid strand has at least 75% complementarity to the first nucleic acid strand, and the first nucleic acid strand and the second nucleic acid strand can complementarily form a double-stranded nucleic acid structure; wherein the saRNA can activate/upregulate the expression of the HMBS gene.

2. The saRNA of claim 1, wherein the first nucleic acid strand and the second nucleic acid strand are present on two different nucleic acid strands.

3. The saRNA of claim 1, wherein the first nucleic acid strand and the second nucleic acid strand are present on the same nucleic acid strand, wherein the saRNA is a hairpin single-stranded nucleic acid molecule, wherein complementary regions of the first nucleic acid strand and the second nucleic acid strand form a double-stranded nucleic acid structure.

4. The saRNA of claim 2, wherein both strands of the saRNA have an overhang of 2 or 3 nucleotides in length at the 3' terminus.

5. The saRNA of claim 1, wherein the first nucleic acid strand and the second nucleic acid strand independently have a length of 16 to 35 nucleotides.

6. The saRNA of claim 4, wherein one strand of the saRNA comprises a sequence having 100% homology or complementarity to a nucleotide sequence selected from SEQ ID NOs:11-20.

7. The saRNA of claim 1, wherein the first nucleic acid strand has at least 90% homology to a nucleotide sequence selected from SEQ ID NOs: 30-39, and the second nucleic acid strand has at least 90% homology to a nucleotide sequence selected from SEQ ID NOs: 49-58.

8. The saRNA of claim 1, wherein said first and second strand is selected from the group consisting of:

SEQ ID NO:30 and SEQ ID NO:49;
SEQ ID NO:31 and SEQ ID NO:50;
SEQ ID NO:32 and SEQ ID NO:51;
SEQ ID NO:33 and SEQ ID NO:52;
SEQ ID NO:34 and SEQ ID NO:53;
SEQ ID NO:35 and SEQ ID NO:54;
SEQ ID NO:36 and SEQ ID NO:55;
SEQ ID NO:37 and SEQ ID NO:56;

SEQ ID NO:38 and SEQ ID NO:57;
SEQ ID NO:39 and SEQ ID NO:58.

9. The saRNA of claim 1, wherein the saRNA comprises at least one chemical modification selected from the group consisting of:

(1) modification of a phosphodiester bond connecting nucleotides in the nucleotide sequence of the saRNA;

(2) modification of 2'-OH of a ribose in the nucleotide sequence of saRNA;

(3) modification of a base in the nucleotide sequence of the saRNA; and (4) at least one nucleotide in the nucleotide sequence of the saRNA being a locked nucleic acid.

10. The saRNA of claim 9, wherein the at least one chemical modification is one or more modification selected from the group consisting of: 2'-fluoro modification, 2'-oxymethyl modification, 2'-oxyethylidene methoxy modification, 2,4'-dinitrophenol modification, locked nucleic acid (LNA), 2'-amino modification, 2'-deoxy modification, 5'-bromouracil modification, 5'-iodouracil modification, N-methyluracil modification, 2,6-diaminopurine modification, phosphorothioate modification, and boranophosphate modification.

11. A nucleic acid coding the saRNA of claim 1.

12. The saRNA of claim 1, wherein the saRNA can activate/upregulate the expression of the HMBS gene by at least 10%.

13. The saRNA of claim 7, wherein said first nucleic acid strand is a first RNA or DNA/RNA hybrid and second nucleic acid strand is a second RNA or a DNA/RNA hybrid.

14. A method for activating/upregulating the expression of HMBS gene in a cell, comprising administering the saRNA of claim 1 to the cell.

15. The method of claim 14, wherein the cell is present in a human body.

16. The method of claim 14, wherein the saRNA is administered to the cell at a final concentration of 1 nM to 150 nM.

17. A method of treating a human patient having a disease or symptom caused by a decreased protein expression of HMBS comprising the step of administering to said patient the saRNA of claim 1.

18. The method of claim 17, wherein said human patient has acute intermittent porphyria.

19. The method of claim 18, wherein the saRNA is administered at a final concentration of 1 nM to 150 nM.

* * * * *